US006727407B1

United States Patent
Tobin et al.

(10) Patent No.: US 6,727,407 B1
(45) Date of Patent: Apr. 27, 2004

(54) NUCLEIC ACIDS ENCODING THE ARABIDOPSIS PROTEIN KINASE β-SUBUNIT CKB3 AND A METHOD OF ALTERING CIRCADIAN RHYTHMS AND FLOWERING IN A PLANT BY TRANFORMING WITH A NUCLEIC ACID ENCODING A PROTEIN KINASE β-SUBUNIT

(75) Inventors: Elaine M. Tobin, Los Angeles, CA (US); Shoji Sugano, Los Angeles, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/359,026

(22) Filed: Jul. 22, 1999

Related U.S. Application Data

(60) Provisional application No. 60/094,072, filed on Jul. 24, 1998.

(51) Int. Cl.[7] ............................ A01H 5/00; C12N 15/29; C12N 15/82
(52) U.S. Cl. ...................... 800/298; 435/419; 536/23.6; 800/278; 800/290; 800/295
(58) Field of Search ..................... 536/23.6; 435/419; 800/278, 286, 290, 295, 298

(56) References Cited

PUBLICATIONS

Collinege et al, Isolation of an Arabidopsis Thaliana Casein Kinase II B Subunit by Complementation in *Saccharomyces cerevisiae*, Jan. 1994, Plant Molecular Biology, vol. 25, pp 649–658.*

David C Baulcombe, RNA as a Target and an Initiator of Post–Transcriptional Gene Silencing in Trangenic Plants, 1996, Plant Molecular Biology, Vol 32, pp 79–88.*

Carter et al, Circadian Rhythms in the Activity of a Plant Protein Kinase. 1991. The EMBO Journal Vol 10, No 8, pp 2063–2068.*

Lee et al 1999, Plant Physiology 119:989–1000.*

* cited by examiner

*Primary Examiner*—Amy J. Nelson
*Assistant Examiner*—David H Kruse
(74) *Attorney, Agent, or Firm*—Reed Smith

(57) ABSTRACT

A gene designated CKB3 whose product interacts specifically with CCA1 has been identified through use of the yeast two-hybrid system. CKB3 is a structural and functional homologue of the regulatory (β) subunit of protein kinase CK2 in Arabidopsis. Recombinant CK2 can phosphorylate CCA1 in vitro. Furthermore, Arabidopsis plant extracts contain a CK2-like activity that affects the formation of a DNA-protein complex containing CCA1. Recombinant plants that overexpress CKB3 have been constructed. Overexpression of CKB3 results in increased CK2 activity and resulted in shorter periods of rhythmic expression of CCA1 and LHY, as well as of four other circadian clock-controlled genes. This resulted a significant shortening of time to flowering under short-day conditions. This change in flowering time was not accompanied by significant phenotypic changes in morphology. Alteration of CK2 activity, particularly through the overexpression of the CKB represents a new and effective way of modulating flowering time in plants.

8 Claims, 15 Drawing Sheets

FIG. 1A-1

```
  1  GTCGACCAC GCGTCCGAGA AGAAAACCCT AGATTTCTCC GTCTCTCTAA TTTCCTTTCT
 61  CTCTCAAGCT TCTCAGAAAG TCTGACACTT TCGAGACACTT AATCTCCAAA TTTCTTGTCT
121  TTTGGAGAA GGAATCGAAT T ATG TAC AAG GAA CGT AGT GGA GGA GGT GGT GGG TCA       13
                              Met Tyr Lys Glu Arg Ser Gly Gly Gly Gly Gly Ser
181  TCG AGA TCA GAG ATC CTC GGT GGA GCT ATT GAT CGG AAA CGA ATC AAC GAT GCA CTC AAT   33
     Ser Arg Ser Glu Ile Leu Gly Gly Ala Ile Asp Arg Lys Arg Ile Asn Asp Ala Leu Asn
241  AAG AAA CTA GAG AAA TCT TCA ACT TCC ACC ACC ACA TCT AGG GTT TTC TCT AAA GAC       53
     Lys Lys Leu Glu Lys Ser Ser Thr Ser Thr Thr Thr Ser Arg Val Phe Ser Lys Asp
301  AAA GAT CCC TTT TCC TTC ACA TCT ACT AAA ACT CAG CTT CCT GAT GTG GAA TCG GAA ACT   73
     Lys Asp Pro Phe Ser Phe Thr Ser Thr Lys Thr Gln Leu Pro Asp Val Glu Ser Glu Thr
361  GAT AGT GAA GGG TCT GAT GTG AGT GGA TCG GAG GGT GAT GAT GAC ACG TGG ATC TCT TGG   93
     Asp Ser Glu Gly Ser Asp Val Ser Gly Ser Glu Gly Asp Asp Asp Thr Trp Ile Ser Trp
421  TTT TGT AAT TTG AGA GGG AAT GAT GGA AAT GAT TTC TGT GAA GTC GAT GAA GAT TAT ATT CAA GAT  113
     Phe Cys Asn Leu Arg Gly Asn Asp Phe Phe Cys Glu Val Asp Glu Asp Tyr Ile Gln Asp
481  GAT TTC AAT CTT TGT GGT TTA AGT GGT CAA GTC CCT TAC TAT GAT TAT GCA CTT GAT CTC   133
     Asp Phe Asn Leu Cys Gly Leu Ser Gly Gln Val Pro Tyr Tyr Asp Tyr Ala Leu Asp Leu
541  ATT TTA GAT GTT GAT GCT TCC AAC AGT GCT GAG ATG TTT ACT GAT GAA CAG CAT GAA ATG GTG  153
     Ile Leu Asp Val Asp Ala Ser Asn Ser Ala Glu Met Phe Thr Asp Glu Gln His Glu Met Val
```

FIG. 1A-2

```
601  GAA TCA GCT GCT GAG ATG CTA TAT GGT CTT ATT CAT GTT CGT TAC ATT TTG ACT ACT AAA    173
     Glu Ser Ala Ala Glu Met Leu Tyr Gly Leu Ile His Val Arg Tyr Ile Leu Thr Thr Lys

661  GGA ATG GCT GCA ATG ACT GAG AAG AAC TAC AAG AAC TGT GAT TTC GGG AGA TGC CCG AGA GTT    193
     Gly Met Ala Ala Met Thr Glu Lys Asn Tyr Lys Asn Cys Asp Phe Gly Arg Cys Pro Arg Val

721  TTC TGT TGC GGT CAG TCT TGT CTT CCA GTT GGA CAA TCC GAT ATC CCG AGA TCG AGT ACT    213
     Phe Cys Cys Gly Gln Ser Cys Leu Pro Val Gly Gln Ser Asp Ile Pro Arg Ser Ser Thr

781  GTG AAG ATA TAC TGC CCT AAA TGC GAG GAT ATA TCT TAC CCG CGA TCT AAA TTC CAA GGC    233
     Val Lys Ile Tyr Cys Pro Lys Cys Glu Asp Ile Ser Tyr Pro Arg Ser Lys Phe Gln Gly

841  AAT ATT GAT GGA GCG TAC TTT GGA ACC ACA TTC CCT CAC TTG TTC TTG ATG ACT TAC GGG    253
     Asn Ile Asp Gly Ala Tyr Phe Gly Thr Thr Phe Pro His Leu Phe Leu Met Thr Tyr Gly

901  AAC TTA AAG CCG CAG AAG CCT ACT CAA AGC TAT GTC CCA AAA ATC TTT GGC TTC AAG GTA    273
     Asn Leu Lys Pro Gln Lys Pro Thr Gln Ser Tyr Val Pro Lys Ile Phe Gly Phe Lys Val

960  CAC AAA CCA TGATACTAGT GCTCTGCATT CTCAATGGTG ATACATTTAG TGGCTCTGTA                  276
     His Lys Pro

1020 ATTGCATCCG GATGAGCAAC TGAAACGATA GCTGCGGGTGA CTGGAGCATA CATCAACCAT T
```

FIG. 1B

```
CKB1 MYRDR....GTVNSRPEV....VDRKRIND........ALER......PS   28
     ||::|    |...||.|:   :|||||||        ||::      .|
CKB3 MYKERSGGGGGGSSRSEILGGAIDRKRIND........ALNKKLEKSSTS   42
     ||:||    |..:|||:   :||||||:         .:....::..:.|
CKB2 MYRER....GMVGSKSEV....VDRKRINEIHDNRPSHSMSQPVNGKGKV   42

CKB1 PSTSRQVNGK...GKGTVTAAT.TTANLIGKQQSNNINHRDSRSASLSKN   74
     ..|||..:|   :|:... .. |...|
CKB3 TTTSRVFSSK...DKDPFSFTS.TKTQL....................   66
     |.||:::..   ||:..|.||.:
CKB2 TSTSVLMGKQQLHDKESSRSGSISKTNI....................   70

CKB1 NTVSDD..ESDTDSEESDVSGSDGEDTSWISWFCNLRGNEFFCEVDDDYI  122
     .|     ||:|||:|||||:|:|||||||||||||||:|||||:|||
CKB3 ...PDV..ESETDSEGSDVSGSEGDDTSWISWFCNLRGNDFFCEVDEDYI  111
     .|.    |:|||:|:|||:|:|||||||||||||||:|||||:|||
CKB2 ...SDAVDISDTDSEESEVSGSDGEDTSWISWFCNLRGNEFFCEVDDDYI  117

CKB1 QDDFNLCGLSSLVPYYEYALDLILDVESSQGEMFTEEQNELIESAAEMLY  172
     ||||||||| : |||:|||||||||:.|..:|||:|:|::||||||||
CKB3 QDDFNLCGLSGQVPYYDYALDLILDVDASNSEMFTDEQHEMVESAAEMLY  161
     ||||||||| |||||:||||||||:.|::||||:||:||:||||||||
CKB2 QDDFNLCGLSHQVPYYDYALDLILDVESSHGEMFTEEQNELIESAAEMLY  167

CKB1 GLIHARYILTSKGLASMLDKYKNYDFGRCPRVYCCGQPCLPVGQSDLPRS  222
     ||||.||||.||:  :|::|||||||||||.||||||||.|||||:|||
CKB3 GLIHVRYILTTKGMAAMTEKYKNCDFGRCPRVFCCGQSCLPVGQSDIPRS  211
     :||.|:|||.||:.|  :||||||||||||.||||||||.||||||||.
CKB2 GMIHARFILTSKGLASMLDKYKNYDFGRCPRVYCCGQPCLPVGQSDIPRA  217

CKB1 STVKIYCPKCEDIYYPRSKYQGNIDGAYFGTTFPHLFLMTYGHLKPAKAT  272
     ||||||||||||:|||||||||||||||||||||||||||||||:| .. :
CKB3 STVKIYCPKCEDISYPRSKFQGNIDGAYFGTTFPHLFLMTYGNLKPQKPT  261
     |||||||||||: ||||:|||||||||||||||||||||||:||||:..
CKB2 STVKIYCPKCEDVYYPRSKYQGNIDGAYFGTTFPHLFLMTYGHLKPQKAS  267

CKB1 QNYVQRVFGFKLHKP                                     287
     |.||..:|||:|||
CKB3 QSYVPKIFGFKVHKP                                     276
     |||..::|||:|||
CKB2 QSYTQRVFGFKLHKP                                     282
```

FIG. 2

SEQ. I.D. No.1

```
GTCGACCCAC GCGTCCGAGA AGAAAACCCT AGATTTCTCC GTCTCTCTAA TTTCCTTTCT    60
CTCTCAAGCT TCTCAGAAAG TCTGACACTT TCGAGAATCT AATCTCCAAA TTTCTTGTCT   120
TTTTGGAGAA GGAATCGAAT TATGTACAAG GAACGTAGTG GAGGAGGTGG TGGTGGGTCA   180
TCGAGATCAG AGATCCTCGG TGGAGCTATT GATCGGAAAC GAATCAACGA TGCACTCAAT   240
AAGAAACTAG AGAAATCTTC AACTTCCACC ACCACATCTA GGGTTTTCTC TTCTAAAGAC   300
AAAGATCCCT TTTCCTTCAC ATCTACTAAA ACTCAGCTTC CTGATGTGGA ATCGGAAACT   360
GATAGTGAAG GGTCTGATGT GAGTGGATCG GAGGGTGATG ATACGTCGTG GATCTCTTGG   420
TTTTGTAATT TGAGAGGGAA TGATTTCTTC TGTGAAGTCG ATGAAGATTA TATTCAAGAT   480
GATTTCAATC TTTGTGGTTT AAGTGGTCAA GTCCCTTACT ATGATTATGC ACTTGATCTC   540
ATTTTAGATG TTGATGCTTC CAACAGTGAG ATGTTTACTG ATGAACAGCA TGAAATGGTG   600
GAATCAGCTG CTGAGATGCT ATATGGTCTT ATTCATGTTC GTTACATTTT GACTACTAAA   660
GGAATGGCTG CAATGACTGA GAAGTACAAG AACTGTGATT TCGGGAGATG CCCGAGAGTT   720
TTCTGTTGCG GTCAGTCTTG TCTTCCAGTT GGACAATCCG ATATCCCGAG ATCGAGTACT   780
GTGAAGATAT ACTGCCCTAA ATGCGAGGAT ATATCTTACC CGCGATCTAA ATTCCAAGGC   841
AATATTGATG GAGCGTACTT TGGAACCACA TTCCCTCACT TGTTCTTGAT GACTTACGGG   900
AACTTAAAGC CGCAGAAGCC TACTCAAAGC TATGTCCCAA AAATCTTTGG CTTCAAGGTA   961
CACAAACCAT GATACTAGTG CTCTGCATTC TCAATGGTGA TACATTTAGT GGCTCTGTAA  1020
TTGCATCCGG ATGAGCAACT GAAACGATAG CTGCGGTGAC TGGAGCATAC ATCAACCATT  1080
```

FIG. 3

SEQ. I.D. No.2

| | | | | | | | | | | | | | | | | | | | | |
|---|---|---|---|---|---|---|---|---|---|---|---|---|---|---|---|---|---|---|---|---|
|Met|Tyr|Lys|Glu|Arg|Ser|Gly|Gly|Gly|Gly|Gly|Ser|Ser|Arg|Ser|Glu|Ile|Leu|Gly|20|
|Gly|Ala|Ile|Asp|Arg|Lys|Arg|Ile|Asn|Asp|Ala|Leu|Asn|Lys|Lys|Leu|Glu|Lys|Ser|Ser|40|
|Thr|Ser|Thr|Thr|Thr|Ser|Arg|Val|Phe|Ser|Ser|Lys|Asp|Lys|Asp|Pro|Phe|Ser|Phe|Thr|60|
|Ser|Thr|Lys|Thr|Gln|Leu|Pro|Asp|Val|Glu|Ser|Glu|Thr|Asp|Ser|Glu|Gly|Ser|Asp|Val|80|
|Ser|Gly|Ser|Glu|Gly|Asp|Asp|Thr|Ser|Trp|Ile|Ser|Trp|Phe|Cys|Asn|Leu|Arg|Gly|Asn|100|
|Asp|Phe|Phe|Cys|Glu|Val|Asp|Glu|Asp|Tyr|Ile|Gln|Asp|Asp|Phe|Asn|Leu|Cys|Gly|Leu|120|
|Ser|Gly|Gln|Val|Pro|Tyr|Tyr|Asp|Tyr|Ala|Leu|Asp|Leu|Ile|Leu|Asp|Val|Asp|Ala|Ser|140|
|Asn|Ser|Glu|Met|Phe|Thr|Asp|Glu|Gln|His|Glu|Met|Val|Glu|Ser|Ala|Ala|Glu|Met|Leu|160|
|Tyr|Gly|Leu|Ile|His|Val|Arg|Tyr|Ile|Leu|Thr|Thr|Lys|Gly|Met|Ala|Ala|Met|Thr|Glu|180|
|Lys|Tyr|Lys|Asn|Cys|Asp|Phe|Gly|Arg|Cys|Pro|Arg|Val|Phe|Cys|Cys|Gly|Gln|Ser|Cys|200|
|Leu|Pro|Val|Gly|Gln|Ser|Asp|Ile|Pro|Arg|Ser|Ser|Thr|Val|Lys|Ile|Tyr|Cys|Pro|Lys|220|
|Cys|Glu|Asp|Ile|Ser|Tyr|Pro|Arg|Ser|Lys|Phe|Gln|Gly|Asn|Ile|Asp|Gly|Ala|Tyr|Phe|240|
|Gly|Thr|Thr|Phe|Pro|His|Leu|Phe|Leu|Met|Thr|Tyr|Gly|Asn|Leu|Lys|Pro|Gln|Lys|Pro|260|
|Thr|Gln|Ser|Tyr|Val|Pro|Lys|Ile|Phe|Gly|Phe|Lys|Val|His|Lys|Pro| | | | |276|

35.5 °C
pKT10
pJCR14
pKT-CKB3
FIG. 4

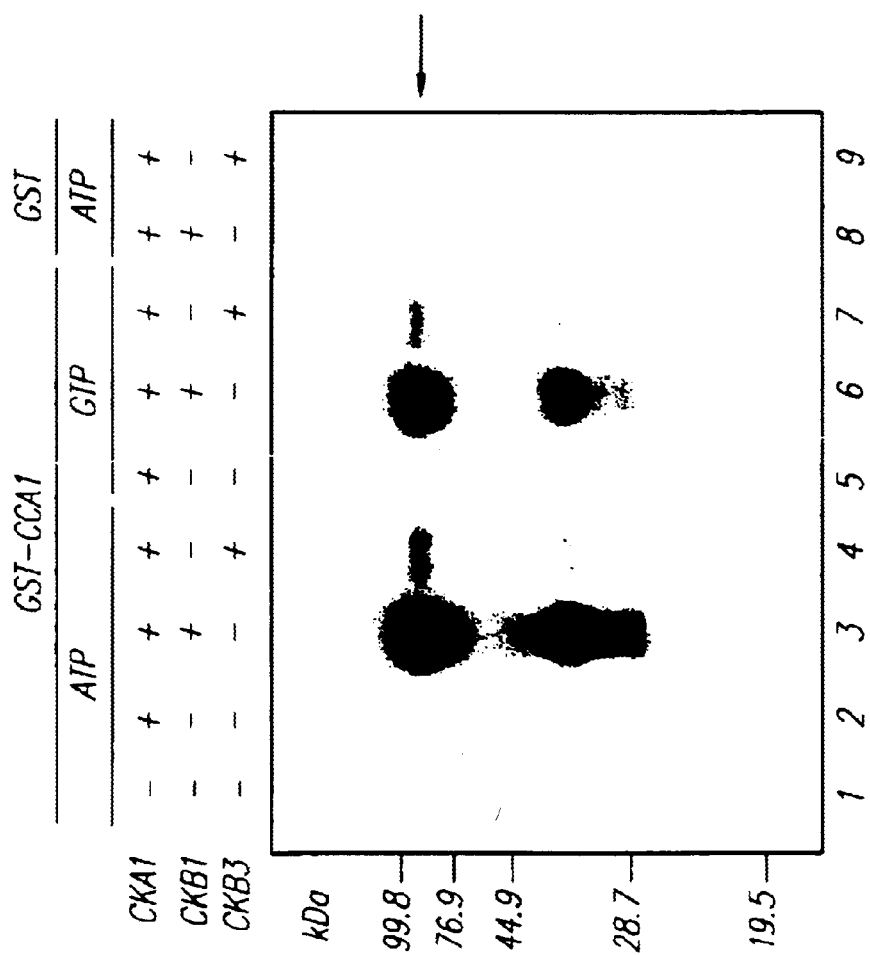
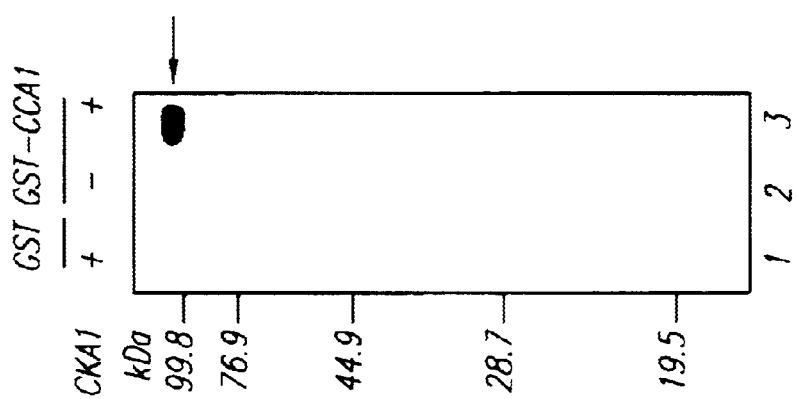
FIG. 7B
FIG. 7A

NUCLEIC ACIDS ENCODING THE ARABIDOPSIS PROTEIN KINASE β-SUBUNIT CKB3 AND A METHOD OF ALTERING CIRCADIAN RHYTHMS AND FLOWERING IN A PLANT BY TRANFORMING WITH A NUCLEIC ACID ENCODING A PROTEIN KINASE β-SUBUNIT

The present application claims benefit of U.S. Provisional Application No. 60/094,072, entitled "A Method or Regulating the Function of a Gene Involved in Circadian Rhythms and Flowering" filed on Jul. 24, 1998.

Research leading to this invention was supported by NIH grant RO1-GM-23167 and the Government may have rights in this patent.

BACKGROUND OF THE INVENTION

1. Field of the Invention

The present application concerns molecular biology and more specifically the molecular components of the "clock" that times biological processes in green land plants.

2. Introduction and Related Art

Endogenous circadian rhythms exist in a wide variety of organisms both multicellular plants and animals as well as microorganisms. Circadian clocks regulating these rhythms consist of input pathways, a central oscillator and output pathways (14, 26, 48). Oscillators are thought to generate rhythms by a transcription-translation negative feedback loop (65, 16, 15, 64, 46). Studies in cyanobacteria, Neurospora, Drosophila and mouse have found that both positive and negative elements that activate and inhibit the transcription of clock genes are required to maintain the feedback loop (16, 15, 64, 46). In addition, postranscriptional and posttranslational regulation play an important role in circadian clocks in Drosophila and Neurospora (65, 51, 57). Input pathways from environmental cues such as light and temperature can entrain the oscillator, and it, in turn, regulates specific cellular events such as expression of clock-controlled genes (14, 26, 48). Until recently, little was known about circadian clocks in plants (33). In *Arabidopsis thaliana*, the toc1 mutant affects the period of many circadian rhythms (37, 52). Although the corresponding gene has not yet been cloned, it is thought that TOC1 encodes a component of the oscillator. The ELF3 gene has been proposed to act in the input pathway (23)

The phytochromes, a class of plant photoreceptors that has been extensively studied (44), regulate the expression of many genes, including the Lhcb genes which encode the chlorophyll a/b-proteins of photosystem II (59). A promoter region of the Lhcb1*3 gene of *Arabidopsis thaliana* that is essential for its regulation by phytochrome was identified (56, 27), and the CCA1 gene, whose product specifically interacts with this promoter region, was cloned (63). The CCA1 gene forms the subject of U.S. patent application Ser. No. 08/843572, filed on Apr. 18, 1997, which is incorporated herein by reference. The motif to which CCA1 binds is highly conserved in promoters of Lhcb genes from many species. Transgenic Arabidopsis plants expressing antisense CCA1 RNA showed reduced phytochrome induction of the endogenous Lhcb1*3 gene in etiolated seedlings. Furthermore, the increase in CCA1 mRNA in response to light preceded the increase in Lhcb1*3 mRNA (63). These data showed that CCA1 is a downstream component of the phytochrome signal transduction pathway leading to increased transcription of the Lhcb1*3 gene in Arabidopsis.

Expression of the Lhcb genes is also regulated by circadian rhythms (36). Characterization of CCA1 has shown that it is also involved in the circadian regulation of the Lhcb1*1 gene and in the control of other physiological rhythms, such as timing of flowering. CCA1 mRNA and protein levels themselves exhibit circadian oscillations, and overexpression of CCA1 repressed the expression of the endogenous CCA1 gene. Our earlier experimental results have demonstrated that the function of CCA1 is closely associated with the circadian oscillator itself (62). LHY, has also been identified as a potential clock genes (49). Constitutive expression of CCA1 was shown to abolish several distinct circadian rhythms and suppress its own expression as well as the rhythmic expression of LHY (61, 62). Lack of CCA1 in a T-DNA insertion mutant line shortened the periods of LHY and other clock-controlled genes (19). Overexpression of LHY also caused photoperiod insensitivity, arrhythmic expression of clock-controlled genes, and reduction of its own expression (49). These data suggest that both CCA1 and LHY may encode components of regulatory negative feedback loops closely associated with the central oscillator. The ESD4 (Early Short Days 4) gene of Arabidopsis is the subject of a patent publication (WO 98/56918) and has also been reported to alter responses to photoperiod.

SUMMARY OF THE INVENTION

To understand how CCA1 may function in the phytochrome signal transduction pathway and in the regulation of circadian rhythms, a yeast two-hybrid system was used to identify proteins that can interact with the CCA1 protein. A gene designated CKB3 whose product interacts specifically with CCA1 has been identified through use of the yeast two-hybrid system. CKB3 is a structural and functional homologue of the regulatory (β) subunit of protein kinase CK2 in Arabidopsis. CK2 is a Ser/Thr kinase that is expressed ubiquitously and consists of two catalytic α- and two regulatory β-subunits. CKB3 and other β-subunits of CK2 interact specifically with CCA1 both in the yeast two-hybrid system and in vitro. Recombinant CK2 can phosphorylate CCA1 in vitro. Furthermore, Arabidopsis plant extracts contain a CK2-like activity that affects the formation of a DNA-protein complex containing CCA1. These results suggest that CK2 can modulate CCA1 activity, and that CK2 may play a role in the regulation of the circadian clock (55, 26, 48).

Recombinant plants that overexpress CKB3 were constructed. Overexpression of CKB3 resulted in increased CK2 activity and resulted in shorter periods of rhythmic expression of CCA1 and LHY, as well as of four other circadian clock-controlled genes. This resulted a significant shortening of time to flowering under short-day conditions. This change is flowering time was not accompanied by significant phenotypic changes in morphology. Alteration of CK2 activity, particularly through the overexpression of the CK β-subunits represents a new and effective way of modulating flowering time in plants.

BRIEF DESCRIPTION OF THE DRAWINGS

FIG. 1 illustrates the structure of Arabidopsis CKB3 and its homology with Arabidopsis CKB1 and CKB2. FIG. 1A shows cDNA sequence and corresponding deduced amino acid sequence of Arabidopsis CKB3. Clone 106 cDNA sequence is underlined. An upstream in-frame stop codon is shown in bold type. Nucleotide numbers are on the left and amino acid numbers on the right. FIG. 1B) illustrates alignment of predicted amino acid sequences of Arabidopsis CKB1, CKB2, and CKB3. Vertical lines indicate identical amino acid residues and conservative amino acid replacements are indicated by single and double dots. Dashes represent gaps introduced to give maximal identity.

FIG. 2 shows SEQ. I.D. No. 1, the cDNA sequence of CKB3 as shown in FIG. 1.

FIG. 3 shows SEQ. I.D. No. 2, the amino acid sequence of CKB3 as shown in FIG. 1.

FIG. 4 is a photograph of culture plates demonstrating compensation of the cka1-Δ1 cka2-8 temperature-sensitive mutation by Arabidopsis CKB3 cDNA. YDH8 (cka1-Δ1, cka2-8) was transformed with yeast expression vectors, and incubated at 25° C. or 35.5° C. Transformants harboring pKT10 vector only, pJCR14 carrying the S. cerevisiae CKB2 gene, and pKT-CKB3 carrying the Arabidopsis CKB3 gene are shown.

FIG. 5 shows the interactions of CCA1 with CK2 subunits.

FIG. 7 shows phosphorylation of CCA1 by CK2 in vitro. FIG. 7A is an autoradiograph of SDS-PAGE analysis which shows that CKA1 can phosphorylate CCA1. GST (lane 1) or GST-CCA1 (lanes 2 and 3) incubated with 280 ng of CKA1 (lanes 1 and 3) or without CKA1 (lane 2) in the presence of [γ-$^{32}$P]ATP. FIG. 7B shows that CK2 β-subunits enhance the phosphorylation of CCA1 by CKA1. GST-CCA1 (lanes 1–7) or GST alone (lanes 8 and 9) was incubated with 14 ng of CKA1 (lanes 2–9) or without CKA1 (lane 1) in the presence of [γ-$^{35}$P]ATP (lanes 1–4, 8, and 9) or [γ-$^{32}$P]GTP (lanes 5–7). Lanes 2 and 5, CKA1 alone; lanes 3, 6, and 8, with 35 ng of CKB1; lanes 4, 7, and 9, with 35 ng of CKB3. Arrows in both panels indicate the position of the full-length GST-CCA1 protein. Other bands might be degradation products of GST-CCA1.

FIG. 9 shows that CK2 phosphorylation is required for the formation of a DNA-protein complex containing CCA1.

FIG. 10 shows that overexpression of CKB3 increases CK2 activity.

FIG. 11 demonstrates that overexpression of CKB3 shortens periods of CCA1 and LHY circadian oscillations.

FIG. 12 illustrates that CK2 can interact with and phosphorylate LHY in vitro.

DETAILED DESCRIPTION OF THE PREFERRED EMBODIMENTS

Figure 5A:
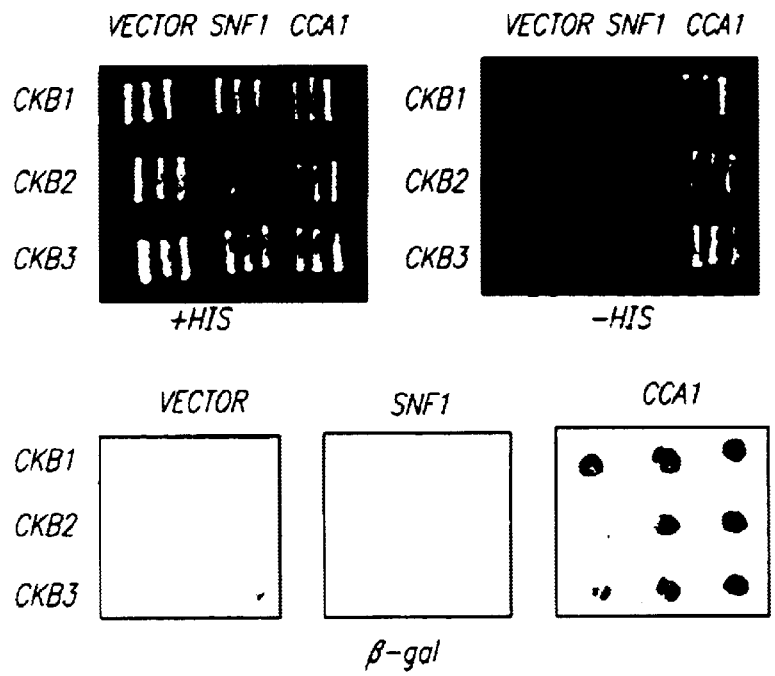
FIG. 5A shows interactions of CCA1 and CKB1, CKB2, and CKB3 in yeast. Each panel shown triplicate patches of yeast expressing GAL4-DB (left lines), GAL4-DB-SNF1 (middle lines), or GAL4-DB-CCA1 (right lines) transformed with GAL4-AD-CKB1 (top rows). GAL4-AD-CKB2 (middle rows), or GAL4-AD-CKB3 (bottom rows). Top left panel (+His), control plate containing histidine; top right panel (−His), plate lacking histidine (selective for the HIS3 reporter gene expression); bottom panel (β-gal), β-galactosidase assay performed on a filter. Dark color shows β-galactosidase activity accumulated after a 3 hr incubation with substrate.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a new method of altering circadian rhythms and flowering in plants through the activation of CK2, particularly by overexpression of β-subunits such as the newly-discovered CKB3.

Standard methods of molecular biology were used in the experiments leading to the present invention. The basic methods are briefly listed below for the edification of one of skill in the art.

Yeast Strains and Expression Plasmid.

*Saccharomyces cerevisiae* Y190 and pAS2, pAS-SNF1, and pACT were obtained from the Arabidopsis Biological Resource Center (ABRC). YDH8 and pJCR14 have been described (20, 45). pKT-CKB3 was constructed by ligating the Arabidopsis CKB3 cDNA into pKT10 (58).

Yeast Two-hybrid Screen and cDNA Isolation.

For the yeast two-hybrid screen, the entire coding region for CCA1 was fused to the GAL4 DNA-binding domain (GAL4-DB) in pAS2. Y190 was transformed with the resulting plasmid, pAS-CCA1, then with a library made from Arabidopsis cDNAs fused to the GAL4 transactivation domain (GAL4-AD) (ABRC). Transformants (4×10$^6$) were analyzed as described previously (11). To obtain a cDNA for the full-length CKB3 gene, an Arabidopsis cDNA library in λgt22 (63) was screened with the selected clone 106. DNA sequencing was done with a Sequenase kit (United States Biochemical). The GenBank database was searched using the BLAST program.

Recombinant Proteins.

pGEX-CCA1 contains cDNA encoding CCA1 cloned into pGEX-3X (Pharmacia). pET-CKA1, pET-CKA2 have been described (39). pT7-CKB1 and pT7-CKB3 contain cDNAs encoding Arabidopsis CKB1 (10) and CKB3 in pT7-His (50). Expression and purification of glutathione-S-transferase (GST) and GST-CCA1 and purification of CCA1 by cleavage of GST-CCA1 with factor Xa have been described (63). CKA1 and CKA2 were produced as described (39), and were purified on a heparin-agarose column (Bio Rad). His-tagged CKB1 and CKB3 were produced in *Escherichia coli* strain BL21 (DE3), and purified on Ni-NTA agarose (Qiagen). Protein concentrations were determined by the Bradford assay (Bio-Rad).

In Vitro Binding Assays.

CK2 subunits and GBF4 labeled with [$^{35}$S]methionine were synthesized by coupled transcription-translation with wheat germ extract (Promega TNT). For in vitro binding, 20 µl of the reactions were added to 200 µl of binding buffer [20 mM Hepes pH 7.6, 100 mM KCl, 10% glycerol, 5 mM EDTA, 0.02% NP40, 1 mM dithiothreitol (DTT), 5 mg/ml bovine serum albumin (BSA)] followed by 10 µl of glutathione-agarose beads with bound GST or GST-CCA1 and incubated at 4° C. The beads were washed with binding buffer, then with binding buffer without BSA. Bound proteins were eluted with 1X SDS-polyacrylamide gel electrophoresis (PAGE) sample buffer and resolved by 12.5% SDS-PAGE. $^{35}$S-labeled bands were detected by autoradiography, and quantitation was performed with a PhosphorImager (Molecular Dynamics).

In Vitro Kinase Assays.

GST-CCA1 bound to glutathione-agarose beads was resuspended in 50 µl of CK2 buffer (50 mM Tris-HCl, pH 7.5, 10 mM MgCl$_2$, 100 mM NaCl, 1 mM DTT. 0.1 mM ATP or GTP) in the presence of 5–10 µCi of [γ-$^{32}$P]ATP or GTP. The reaction was started by adding CK2 or whole-cell extracts (WCE) and incubating samples at 30° C. for 30 min. WCE were prepared as described previously (3) except that the phosphatase inhibitor cocktail (5 mM NH$_4$VO$_3$, 0.2 mM ammonium molybdate, 1 mM EGTA, 50 mM NaF) was added to extraction buffer. The beads were washed with phosphate-buffered saline (PBS) containing 1% Triton X-100 and resuspended in 1X SDS-PAGE sample buffer. The phosphorylated samples were separated by 10% SDS-PAGE. $^{32}$P-labeled bands were detected by autoradiography and quantitated with a PhosphorImager.

Electrophoretic Mobility Shift Assays (EMSA).

CCA1 was incubated with 0.1 ng of end-labeled A2 fragment of the Arabidopsis Lhcb 1*3 gene (56) in the presence of 0.5 µg of poly(dI-dC) at 25° C. for 15 min. WCE were incubated in preincubation buffer (50 mM Tris-HCl, pH 7.5, 2 mM MnCl$_2$, 5 mM DTT, 0.1 mM EDTA, 0.01% Brij 35) at 30° C. for 45 min, then incubated with the A2 probe in the presence of 1 µg of poly(dI-dC). The EMSA buffer and electrophoresis conditions have been described (56). DNA-protein complexes were detected by autoradiography.

The following results were obtained using the above methods.

Isolation and Analysis of the CKB3 cDNA.

To isolate proteins that interact with CCA1, the yeast two-hybrid system that uses GAL4 recognition sites to regulate expression of both HIS3 and lacZ genes was used (21). The GAL4-DB-CCA1 fusion protein did not itself activate transcription of the reporter genes. Four positive colonies were obtained which contained plasmid that activated HIS3 and lacZ transcription only in the presence of GAL4-DB-CCA1. These fell into two classes based on sequence analysis, and one of them, clone 106, was fully characterized.

The reading frame of clone 106 encoded a 214 amino acid fragment. Because a putative translation initiation codon was missing in this cDNA clone, corresponding clones were isolated from an Arabidopsis cDNA library. The sequence of the full-length cDNA insert is shown in FIG. 1A. The 276 amino acid residues open reading frame encodes an estimated 30.8 kDa protein. The first ATG codon of the open reading frame starts at 142 bp and is preceded by an in-frame stop codon at the −42 to −40 position and by a purine (A) at the −3 position. This is a favorable context for an initiation codon in plants (32). The deduced amino acid sequence is highly homologous to the β-subunit of protein kinase CK2, in particular to Arabidopsis CKB1 and CKB2. Thus, the gene corresponding to this cDNA clone was designated CKB3. The nucleic acid sequence is separately illustrated as SEQ. I.D. No. 1 in FIG. 2 while the amino acid sequence is separately illustrated as SEQ. I.D. No. 2 in FIG. 3.

Figure 10A:
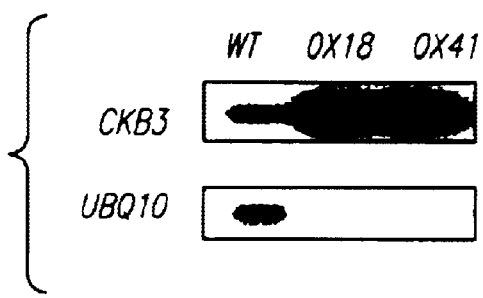
FIG. 10A shows gel results of a quantitative RT-PCR analysis of CKB3 and UBQ10 transcript levels in wild-type (WT) and independent homozygous transgenic lines (ox18 and ox41) after 14 days growth under L:D 16:8 photoperiods. PCR products were detected by Southern blotting using $^{32}$P-labeled probes. The UBQ10 transcript levels were used as an internal control.
Figure 10B:
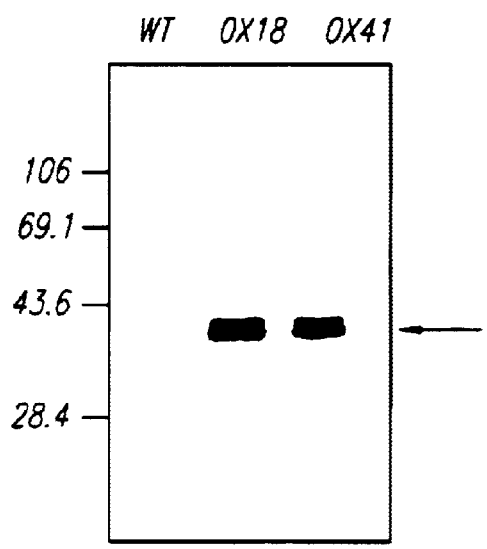
FIG. 10B shows a Western blot analysis of CKB3 levels in transgenic lines grown as in FIG. 10A. The c-myc-tagged CKB3 protein (arrow) was detected with monoclonal anti-c-myc antibody. Other bands are non-specific. Molecular size markers are given to the left in kiloDaltons.

FIG. 10B shows an alignment of the amino acid sequences of Arabidopsis CKB1. CKB2, and CKB3. The amino acid identities between CKB3 and CKB1, CKB3 and CKB2, and CKB1 and CKB2 are 75%, 71% and 80%, respectively. The similarity is greatest over the carboxyl-terminal two thirds of the three proteins. The CKB3 protein shares most of the structural features of CKB1 and CKB2 at the level of primary structure (10). First, CKB3 contains a potential metal-binding motif Cys-Pro-$X_3$-Cys-$X_{22}$-Cys-Pro-X-Cys (SEQ. I.D. No. 3) (45) (wherein "X" may be any amino acid). Second, although the conserved autophosphorylation site, Ser-Ser-Ser-Glu-Glu (SEQ. I.D. No. 4), is missing in the amino-terminal region of CKB3, there are two CK2 recognition phosphorylation sites. $^{81}$Ser-Gly-Ser-Glu-Gly-Asp (SEQ I.D. No. 5) and $^{83}$Ser-Glu-Gly-Asp-Asp, (SEQ I.D. No. 6) in about the same location as in the animal β-subunits. Third, CKB3 has an N-terminal extension preceding the putative phosphorylation sites which exhibits a moderate level of similarity to the N-terminal extension of the other Arabidopsis β-subunits. Neither yeast nor animal β-subunits contain such an N-terminal extension, and this region bears no extensive similarity to other proteins. CKB3 has functional similarity to CKB1 and CKB2.

S. cerevisiae has two genes coding for the catalytic (α) subunits of CK2, and at least one of the two genes is required for vegetative growth. YDH8, which carries the cka1-Δ1 cka2-8 mutation, grows at 25° C., but not at 35.5° C. (20), and this temperature sensitivity can be compensated for by overexpressing CK2 β-subunits, including Arabidopsis CKB1 and CKB2 (10). We tested whether CKB3 could also compensate for the temperature sensitivity of the mutation. As controls, pKT10 and pJCR14, which contains the S. cerevisiae CKB2 gene, were also transformed into YDH8. FIG. 4 shows that YDH8 cells expressing either S. cerevisiae CKB2 or Arabidopsis CKB3 could grow both at 25° C. and 35.5° C., while transformants with pKT10 could grow only at 25° C. These results demonstrate that CKB3 shares functional similarity with CKB1 and CKB2.

CCA1 can interact with both α- and β-subunits of CK2.

Although CKB1, CKB2, and CKB3 share a high degree of structural and functional homology, it might be that CKB3 is the only β-subunit that associates with CCA1 specifically. Therefore, we tested whether CKB1 and/or CKB2 are also able to interact with CCA1 in the yeast two-hybrid system and confirmed that the full-length CKB3 could interact with CCA1 in the same way as the product of the original cDNA clone. FIG. 5A demonstrates that CKB1, CKB2 and CKB3 can each interact specifically with CCA1 in yeast.

Figure 5B:
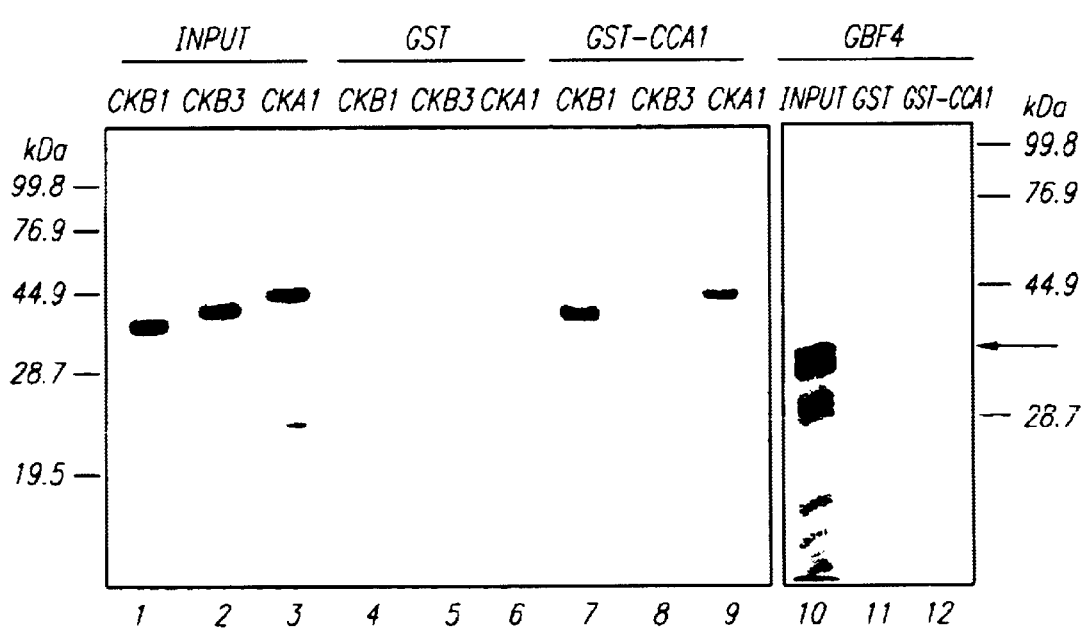
FIG. 5B is an autoradiograph of SDS-PAGE analysis showing in vitro interactions between CKB1, CKB3, CKA1 and CCA1. GST-CCA1 or GST immobilized on glutathione-agarose beads was mixed with $^{35}$S-labeled CKB1, CKB3, CKA1 or GBF4. The amount of proteins bound to GST (lanes 4–6, 11), or GST-CCA1 (lanes 7–9, 12) is shown. Lanes 1–3, and 10 represent 5% of the $^{35}$S-labeled proteins used.

To further investigate the direct interaction of CCA1 with β-subunits of CK2, the ability of GST-CCA1 to bind to CK2 β-subunits in vitro was also tested. FIG. 5B shows that CKB1 and CKB2 bound to GST-CCA1 efficiently but not to GST alone (lanes 4 and 7). CKB3 also interacted with GST-CCA1, but apparently less efficiently than did CKB1 and CKB2 (lane 8). Similar analyses showed that CKA1 and CKA2, the two α-subunits of CK2 (39), also bound to GST-CCA1 (lane 9). While it is possible that CK2 β-subunits that could be present in the wheat germ extract might mediate the interaction of CCA1 with the CK2 α-subunit, our results suggest that CCA1 can interact with both CK2 α-subunits and β-subunits in vitro. As a negative control in these experiments, GBF4, a bZIP transcription factor (35), was used. GBF4 did not show a specific interaction with GST-CCA1 (lanes 11 and 12), confirming that the interaction of CCA1 with CK2 subunits is specific.

CK2 can stimulate binding of CCA1 to the Lhcb1*3 promoter in vitro.

Figure 6:
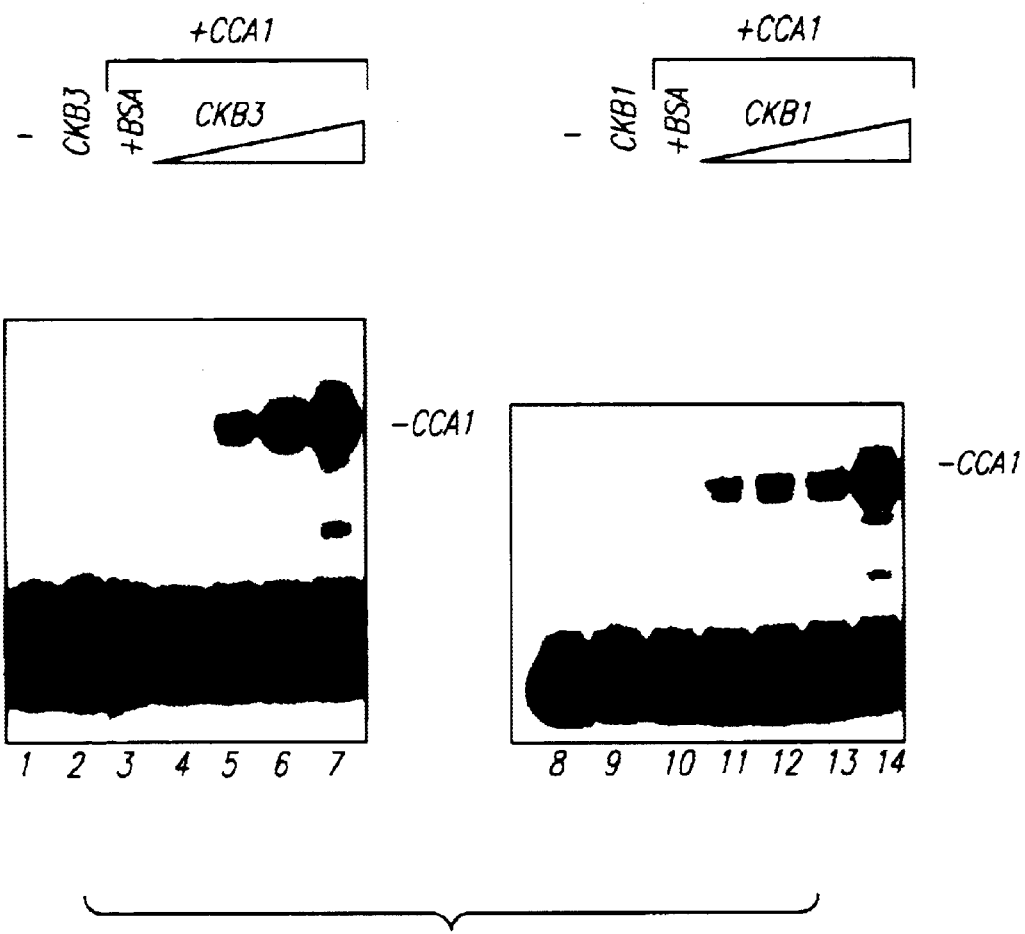
FIG. 6 illustrates that CK2 β-subunits enhance the binding of CCA1 to the Lhcb1*3 promoter. Autoradiographs of the EMSA are shown. The $^{32}$P-labeled A2 fragment was incubated with 0.5 ng of CCA1 in the presence of increasing amounts of His-tagged CKB3 (left panel) or CKB1 (right panel) (lanes 4 and 11, 1 ng; lanes 5 and 12, 2 ng; lanes 6 and 13, 5 ng; lanes 7 and 14, 10 ng). Lanes 1 and 8, probe alone; lanes 2 and 9, the A2 fragment with 50 ng of CKB3 and CKB1; lanes 3 and 10, the A2 fragment with 0.5 ng of CCA1 and 50 ng of BSA.

The possible biochemical consequences of the interaction of CK2 β-subunits with CCA1 were examined. First, we tested whether DNA binding activity of CCA1 was affected by its interaction with CK2 β-subunits. As shown in FIG. 6, binding of CCA1 to the A2 fragment was stimulated specifically by CKB3 at low concentrations of CCA1 (lanes 3–7). CKB3 did not itself show any binding to the probe (lane 2) CKB1 also enhanced DNA binding activity of CCA1 in the same way (lanes 10–14).

CK2 can phosphorylate CCA1 in vitro.

A second approach to understand the function of the CK2-CCA1 interaction was to determine whether recombinant CK2 can phosphorylate CCA1 in vitro. CCA1 has several putative sites for phosphorylation by CK2. We initially tested phosphorylation of CCA1 by CKA1, one of the α-subunits of CK2. FIG. 7A shows that a large amount of CKA1 (280 ng) phosphorylates GST-CCA1 but not GST (lanes 1 and 3). It has been shown that CK2 β-subunits stimulate the catalytic activity of α-subunits toward most substrates (42, 24, 1,). FIG. 7B shows that when a smaller amount (14 ng) of CKA1 was used, a strong stimulation of the CCA1 phosphorylation was observed by adding either CKB1 or CKB3 (lanes 2–4). Similar results were obtained for CKA2, the other α-subunit of CK2 (data not shown). FIG. 7B also shows that CCA1 could be phosphorylated in the presence of GTP as well as in the presence of ATP (lanes 5–7). These data confirm that the phosphorylation can be attributed to CK2 activity, because CK2 is unique among protein kinases in that it can use both ATP and GTP as a phosphodonor.

Phosphorylation by CK2 has been shown to affect the DNA binding activity of many transcription factors. Therefore, the possible effect of CK2 phosphorylation on the DNA binding activity of CCA1 was examined. When recombinant CCA1 was phosphorylated by CK2, no effect on its DNA binding activity was observed in the EMSA assay (data not shown).

Arabidopsis plants contain a CK2-like activity that can phosphorylate CCA1 in vitro.

Figure 8:
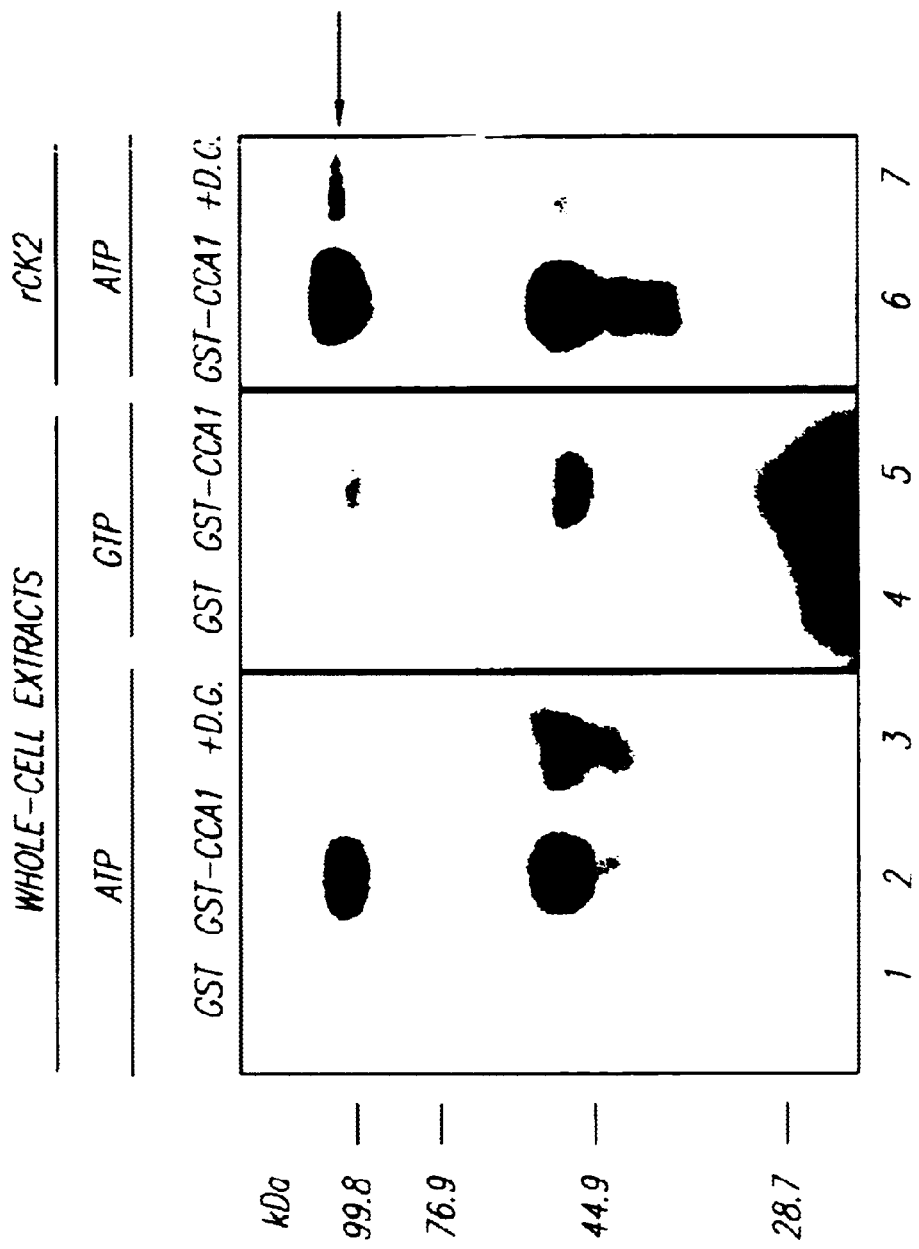
FIG. 8 demonstrates that Arabidopsis plants contain a CK2-like activity that phosphorylates CCA1 in vitro. GST (lanes 1 and 4) or GST-CCA1 (lanes 2, 3, 5–7) were incubated with 160 μg of WCE in the absence (lanes 1, 2, 4, and 5) or presence (lane 3) of 10 mM 2,3-diphosphoglycerate (D. G.), with recombinant CK2 (rCK2) in the absence (lane 6) or presence of 10 mM 2,3-diphosphoglycerate (lane 7) together with [γ-$^{32}$P]ATP (lanes 1–3, 6, and 7) or [γ-$^{32}$P]GTP (lanes 4 and 5). The arrow indicates the position of the full-length GST-CCA1 protein.

We next examined whether plants contain a CK2-like protein kinase activity that can phosphorylate CCA1 in vitro. FIG. 8 shows that GST-CCA1, but not GST alone, was phosphorylated by a kinase activity in Arabidopsis whole-cell extracts in vitro (lanes 1 and 2). FIG. 8 also shows that this kinase activity was able to utilize both ATP and GTP as a phosphodonor (lane 5). Furthermore, addition of 2,3-diphosphoglycerate, which is an inhibitor of CK2 (18), reduced the incorporation of ATP into GST-CCA1 by 63% (lane 3). When this inhibitor was added to recombinant CK2, the phosphorylation of CCA1 was reduced by 77% (lane 7).

These results demonstrate that the Arabidopsis plants contain a CK2-like activity that phosphorylates CCA1 in vitro, and that this kinase activity is responsible for much of the phosphorylating activity on CCA1 in the extracts. Phosphorylation by CK2 is required for formation of the DNA-protein complex containing CCA1 in plant extracts.

Figure 9C:
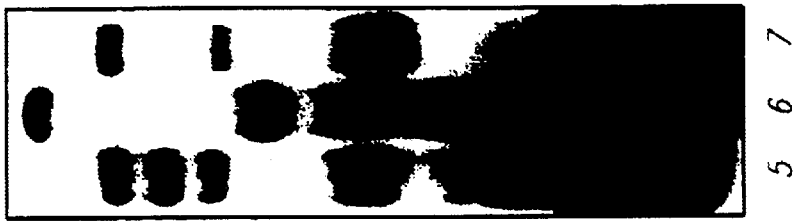
FIG. 9C shows that inhibition of CK2 activity in plant extracts abolishes CCA1 binding. WCE were incubated with the indicated inhibitor for 45 min at 30° C. Lane 1, no inhibitors; lane 2, 5 mM 2,3-diphosphoglycerate (D.G.); lane 3, 100 μM quercetin. Arrows indicate the position of the major DNA-protein complex containing CCA1.
Figure 9B:
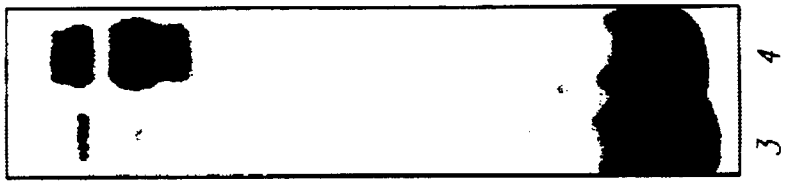
FIG. 9B shows that the CCA1 containing complex is more abundant in plants overexpressing CCA1 than in wild type. WCE from wild type (WT) and a CCA1-ox line (CCA1-ox) (7) grown in 12:12 photoperiods were used in the EMSA.
Figure 9A:
FIG. 9A shows that phosphatase treatment abolishes CCA1 binding. WCE were incubated in the absence (lane 1) or presence (lane 2) of λ protein phosphatase (200 units added to 200 μl) for 30 min at 30° C.

FIG. 9A shows that the DNA binding activity of the major CCA1-containing complex in plant extracts depends on phosphorylation. When the extracts were treated with λ protein phosphatase, formation of the complex was inhibited completely. The major DNA-protein complex containing CCA1 (marked with arrows) migrated more slowly than that formed with recombinant CCA1, suggesting that other proteins in the plant extracts are included in this complex, interacting with CCA1 and/or binding to the DNA. The A2 fragment used as a probe includes known binding sites for G-box and CAAT binding proteins (56). FIG. 9B shows that this complex is more abundant in extracts of plants expressing CCA1 under the control of a constitutive promoter (62). Further evidence that the marked complex contains CCA1 includes the observations (data not shown) that this complex is absent in extracts prepared from CCA1-null mutant plants and that addition of anti-CCA1 antibodies inhibits its formation. FIG. 9C demonstrates that the CK2-like phosphorylation activity in the extracts is important for this binding activity. Formation of the complex was abolished when CK2 inhibitors, either 2,3-diphosphoglycerate or quercetin, were added to the preincubation reactions. 2,3-diphosphoglycerate inhibits both CK1 and CK2, whereas inhibition by quercetin is specific to CK2 (18, 9). The components of the new bands that appear in the inhibitor treated samples are not yet known, but these bands presumably represent a change in the composition of the CCA1-containing complex in the absence of GK2-mediated phosphorylation. Taken together, these results demonstrate that phosphorylation by CK2 is required in the plant extracts for formation of the major DNA-protein complex containing CCA1.

The protein kinase CK2 is a Ser/Thr kinase that is ubiquitously expressed and highly conserved (42, 24, 1). CK2 consists of two catalytic ($\alpha$) and two regulatory ($\beta$) subunits, which form an $\alpha_2\beta_2$ heteromeric holoenzyme. Although most organisms have two genes encoding $\alpha$-subunits and one gene encoding the $\beta$-subunit, two genes encoding $\beta$-subunits have been reported in S. cerevisiae and Arabidopsis (45, 10, 3). The CKB3 protein exhibits significant amino acid sequence identity with Arabidopsis CKB1 and CKB2. Several lines of evidence confirm that CKB3 does indeed function as a third CK2 $\beta$-subunit in Arabidopsis. First, CKB3 was able to compensate for the temperature-sensitive growth defect of an S. cerevisiae cka1-Δ1 cka2-8 mutation. Second, recombinant CKB3 was able to stimulate the catalytic activity of CKA1 when CCA1 was used as a substrate. CKB3 is the only reported example of a third CK2 $\beta$-subunit in any organism. Interestingly, it had been suggested previously that there might be a third CK2 $\alpha$-subunit in Arabidopsis (39). It is yet to be determined whether there are several forms of the holoenzyme with different subunit compositions or whether different subunits confer different substrate specificities and/or tissue specificities.

We have shown that CK2 $\beta$-subunits specifically interact with CCA1 both in yeast and in an in vitro interaction assay. We did not isolate clones for the two other CK2 $\beta$-subunits in the initial screen, but we have observed that the growth of yeast containing the constructs for these subunits is slower than that of cells expressing the CAL4-AD-CKB3 construct, and this may account for our failure to identify them along with CKB3.

We have found that recombinant His-tagged CK2 $\beta$-subunits stimulate binding of CCA1 to a fragment of the Lhcb1*3 gene. This effect is likely to be specific because OBP1, a DNA binding protein that stimulates interaction of OBF4 and OBF5 with ocs elements, did not affect binding of CCA1 to the A2 fragment (66). Also, both recombinant GST-CKB1 and GST-CKB3 stimulated DNA binding of CCA1, whereas GST alone had no effect (data not shown), demonstrating that CK2 $\beta$-subunits are responsible for the enhancement. The fact that the mobility of the complex was not affected suggests that the interaction of the proteins might be transient or unstable under the conditions for the EMSA. There have been other such reports of enhancement of DNA binding by a second protein without altering the mobility of the DNA-protein complex (66, 60, 31, 11).

The fact that CK2 $\beta$-subunits associate with CCA1 and stimulate its binding to the Lhcb1*3 promoter suggests a different mechanism for regulation of CCA1 DNA binding activity other than phosphorylation. In fact, the $\alpha$-subunit is not required for this stimulation, and CK2 $\beta$-subunits cannot themselves phosphorylate CCA1. It is possible that in addition to being the regulatory subunit of CK2, the $\beta$-subunit might play other roles in the cell. Overexpression of the CK2 $\beta$-subunit in Schizosaccharomyces pombe causes multiple septation and inhibits cell growth and cytokinesis (47). These phenotypes appeared to be due to the production of free $\beta$-subunit rather than to excess holoenzyme. In Xenopus oocytes, the $\beta$-subunit interacts with Mos, a germ cell-specific Ser/Thr kinase that is required for oocyte maturation, and this interaction negatively regulates Mos-mediated mitogen-activated protein kinase activation resulting in repression of oocyte maturation (7, 6). Recently, it was also shown that cyclin D, which is a regulatory component of complexes of cyclin with cyclin dependent kinase (Cdk), stimulates transcriptional activity of estrogen receptor independent of interaction with Cdks (67). Therefore, it is intriguing to speculate that direct interaction of CK2 $\beta$-subunits with CCA1 stimulates binding of CCA1 to promoter sequences and can affect CCA1-mediated transcription.

We have demonstrated that CKA1 phosphorylates CCA1 in vitro and that both CKB1 and CKB3 stimulate this phosphorylation. Although CKA1CKB1 showed a higher activity of CCA1 phosphorylation than CKA1CKB3, the possibility that this was due to differing relative activities of CKB1 and CKB3 in their corresponding preparations cannot be excluded. We have also demonstrated that Arabidopsis plants contain a CK2-like protein kinase activity that can phosphorylate CCA1 in vitro, and that this is a major kinase activity for CCA1 phosphorylation in the extracts. The identity of this kinase was confirmed in two ways. First, the kinase activity phosphorylates CCA1 in the presence of GTP as well as ATP, a unique characteristic that distinguishes CK2 from other Ser/Thr kinases. Second, addition of 2,3,-diphosphoglycerate, an inhibitor of CK2, inhibited most of the CCA1 phosphorylating activity in the plant extracts.

Phosphorylation of transcription factors by CK2 has been reported to modulate their DNA binding activity, cellular localization, metabolism, and interaction with other proteins (1, 12, 28, 40, 2, 25, 34, 41). It was recently shown that the Lhcb1*1 RNA level in transgenic plants overexpressing CCA1 decreased steadily when plants were transferred from light-dark cycles into constant dark even though CCA1 was expressed at a high level (62). We have also observed that the Lhcb1*1 RNA level in etiolated transgenic plants overexpressing CCA1 was as low as that in etiolated wild type plants (data not shown). These observations suggest that CCA1 activity is regulated by light through posttranslational modifications, one of which could be phosphorylation. In this regard, our finding that plant extracts contain a CK2-like activity that is required for formation of the major DNA-protein complex containing CCA1 is especially noteworthy. The CCA1-containing complex is likely to contain a protein or proteins in addition to CCA1. Although CK2 phosphorylation of recombinant CCA1 did not affect its DNA binding acitvity in vitro, it is possible that in the plants the other proteins affect the relative binding affinities of the phosphorylated and non-phosphorylated forms of CCA1 for its binding sites. Alternatively, the phosphorylation state of CCA1 might be important for protein-protein interactions of CCA1 with other protein(s) in the complex, it is also possible that phosphorylation of other protein(s) by CK2 is essential for the CCA1 complex formation.

Overexpression of CKB3

To further explore the hypothesis that the CK2-CCA1 DNA-protein complex plays a role in the regulation of the circadian clock, we created transgenic Arabidopsis plants overexpressing a c-myc tagged form of CKB3 and analyzed their circadian behavior. To produce the tagged CKB3 an Eco R[-Bsr G] fragment of the plasmid pUC-CKB3 that contains the entire coding sequence of CKB3 cDNA at the Bam HI site of pUC19 was replaced with the duplex DNA composed of oligonucleotide myc-CKB3F (5'-AATTGAGATCTCATGGAGCAAAAGCT-TATCAGCGAGGAGGACTT GAACAT) (SEQ I.D. No. 7) and oligo-nucleotide myc-CKB3B (5'-GTACATGTTCAAGTCCTCCTC GCTGATAAGCTTTTGCTCCATGAGATCT) (SEQ I.D. NO. 8) to introduce the Bgl II site and c-myc encoding sequence in front of CKB3. The resultant plasmid was digested with Bgl II and Hinc II, and the Bgl II-Hinc II fragment was subcloned into the pBII21 vector (Clonetech). This construct was used to transform *Agrobacterium tumefaciens* strain A2260, and then Arabidopsis plants (Columbia ecotype) using the in planta transformation procedure as described (61, 62). Overexpression of CKB3 had no apparent effects on plant growth and development except timing of flowering.

From 16 transgenic lines that each had a single site of insertion, two transgenic lines designated ox18 and ox41 were further analyzed. Levels of CKB3 transcript in the fourth generation of homozygous CKB3-overexpressing (CKB3-ox) plants were approximately 20 times higher than that in the wild-type (FIG. 10A). Ten µg of total RNA were treated with RQ1 RNase-free DNase (Promega) and the first-strand cDNA was synthesized as described in (43) The product of the first-strand synthesis was then used for PCR to amplify 140 bp CKB3 cDNA with the primers CKB3F1 (5'-ACAAGGAACGTAGTGGAGGAGGTG) (SEQ I.D. No. 9) and CKB3B3 (5'-AACCCTAGATGT GGTGGTGGAAG) (SEQ I.D. No. 10). As a control, primers UBQ10-5' and UBQ10-3' (61, 62) were used to amplify 111 bp UBQ10 cDNA. The resultant PCR fragments were separated on a 2% agarose gel, blotted and hybridized with $^{32}$P-labeled probes.

Figure 10C:
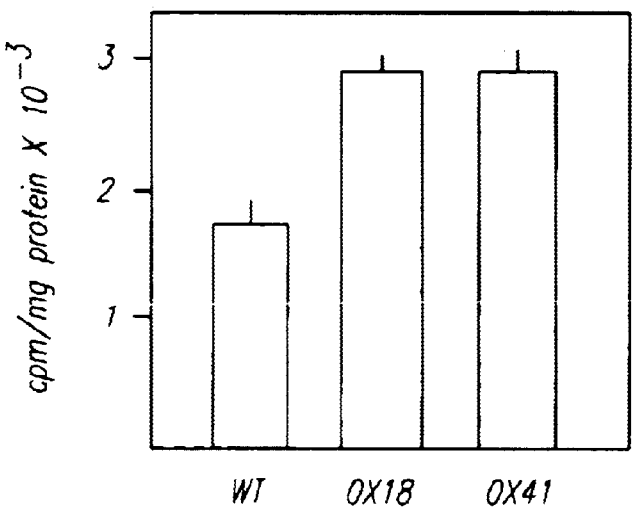
FIG. 10C shows a graph of CK2 activity in plant extracts prepared from wild-type and CKB3-ox lines. Plants were grown for 20 days under continuous white light. The data shown are means of two independent experiments for each line with the range of the measurements indicated.

The transgenic plants contained appreciable amounts of the c-myc-tagged CKB3 protein (FIG. 10B). Protein extracts were obtained by grinding 10-day-old seedlings in 100 µl of 3XSDS-sample buffer (180 mM Tris-HCl (pH 6.8), 6% SDS, 30% glycerol, 7.5% 2-mercaptoethanol), boiling this mixture for 5 min and saving the supernatant after centrifugation for 15 min at 14,000×g. Protein concentration was measured with a protein assay reagent (Bio-Rad). Western blots were performed using anti-c-myc monoclonal antibody 9E10 (17, 15, 64, 46) following the methods described in (61, 62). Measurement of CK2 activity in whole-cell extracts showed that the transgenic lines exhibited a 1.7-fold increase in CK2 activity (FIG. 10C). Frozen seedlings (100 mg) were ground and extracted with 100 µl of extraction buffer (50 mM Tris-HCl (pH 7.5). 15 mM $MgCl_2$, 0.1 M KCl, 0.25 M sucrose and 10% glycerol, 1 mM phenylmethylsulfonylfluoride, protease inhibitor cocktail (Boehringer Mannheim), phosphatase inhibitor mixture (55, 26, 48) and 14 mM 2-mercaptoethanol). After centrifugation at 14,000×g for 15 min. the supernatant was saved and protein concentration was measured as above. CK2 assays were carried out at 37° C. with 200 µM CK2 specific peptide substrate Arg-Arg-Arg-Asp-Asp-Asp-Ser-Asp-Asp-Asp (SEQ I.D. No. 11) (Boehringer Mannheim) in 25 µl of CK2 buffer (55, 26, 48) as described (5).

Figure 11A:
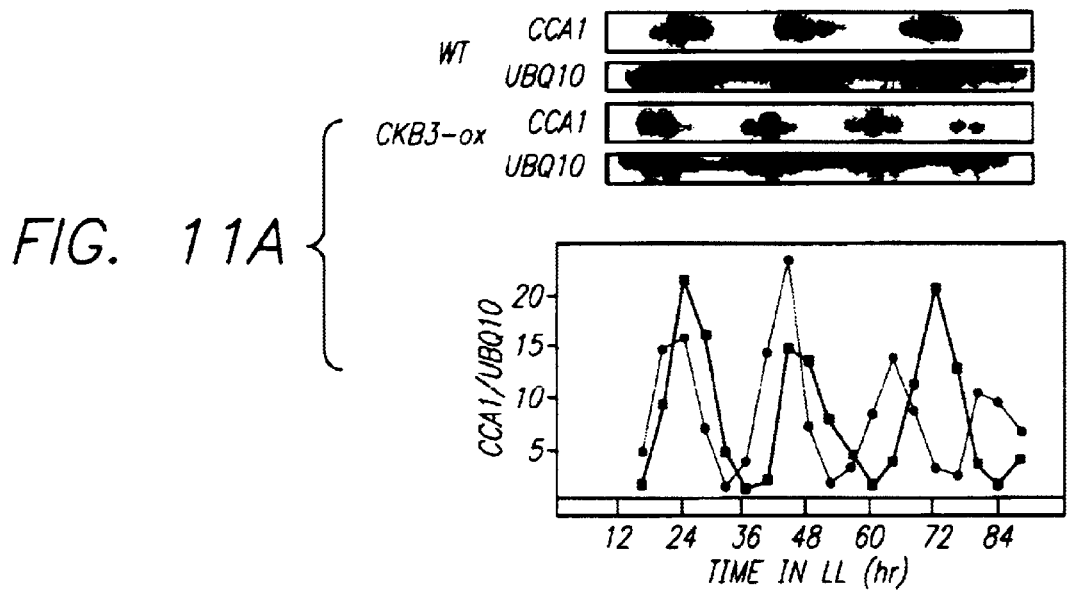
FIG. 11A shows gel electrophoresis demonstrating Circadian oscillation of CCA1 expression in wild-type and CKB3-ox (line ox18) plants. Plants were grown for 12 days in L:D 12:12 photoperiods then transferred to continuous light after light-on of day 13. After 16 h, tissue was collected every 4 h. Total RNA was isolated and analyzed for CCA1 transcripts by Northern blot analysis with $^{32}$P-labeled probes. The UBQ10 RNA levels were used as an internal control for quantitation. A representative autoradiogram is shown in the upper panel. The lower panel shows the quantitation of one RNA blot. Values were normalized to the lowest value of the wild-type samples. Closed squares (solid line), wild-type: circles. CKB3-ox. The bar represents the subjective light conditions for the wild-type plants. Experiments were performed three times with similar results. The same results were also obtained in another CKB3-ox line (ox41).
Figure 11B:
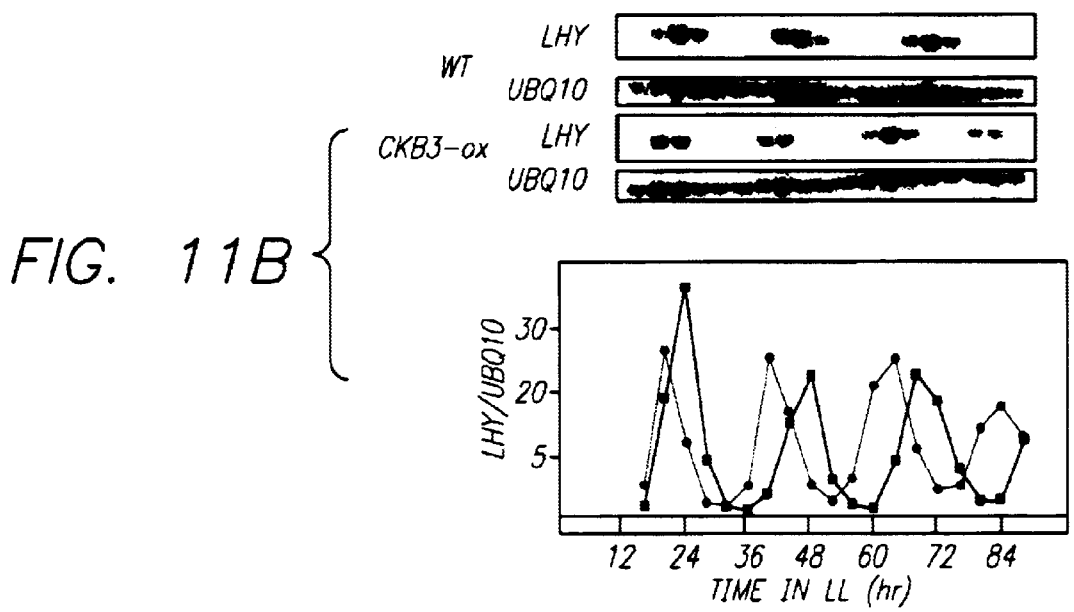
FIG. 11B illustrates gels showing circadian oscillation of LHY in wild-type and CKB3-ox plants. LHY transcripts in the same RNA samples were analyzed as in FIG. 11A.
Figure 11C:
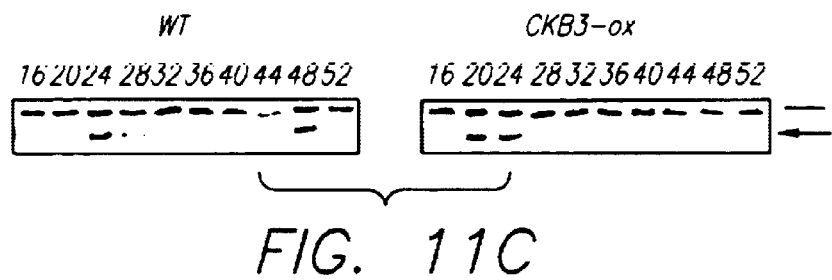
FIG. 11C illustrates CCA1 protein levels in wild-type and CKB3-ox (line ox18) plants. Proteins extracted from the same tissue as used for RNA preparation were analyzed by Western blotting and detected with anti-CCA1 antibody (8). The arrow and line indicate CCA1 and nonspecific cross-reading proteins, respectively. Experiments were repeated twice with similar results.

We next examined whether CKB3 overexpression affected circadian expression of the CCA1 and LHY genes. Oscillations in expression of these genes are robust in wild-type plants transferred into continuous light. FIGS. 11A and 11B show that the periods of CCA1 and LHY RNAs were shortened by about four hours in the CKB3-ox plants (total RNA isolation and RNA blot analyses were performed as described in (61, 62, 19)), and no differences in the amplitude of the rhythms were seen. FIG. 11C shows that the period of the CCA1 protein oscillation was also shortened (immunoblot analyses of the CCA1 protein were carried out as explained in (61, 62)). Thus, overexpression of CKB3 affected circadian rhythms of these two genes that are closely associated with the circadian clock.

Figure 12A:
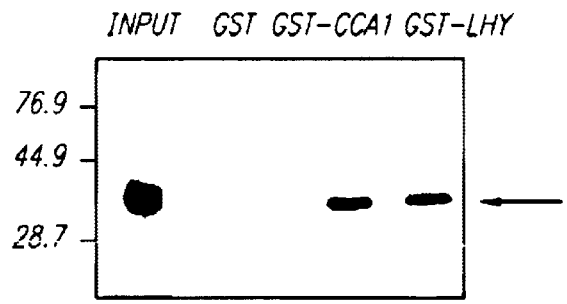
FIG. 12A shows interaction of LHY with CKB3 in vitro. $^{35}$S-labeled CKB3 was mixed with GST, GST-CCA1 or GST-LHY immobilized on glutathione-agarose beads. Bound proteins were analyzed by 12.5% SDS-PAGE. The input lane represents 10% of the 35S-labeled CKB3 used and the other lanes show the amount of bound CKB3. Molecular size markers are given to the left in kiloDaltons.
Figure 12B:
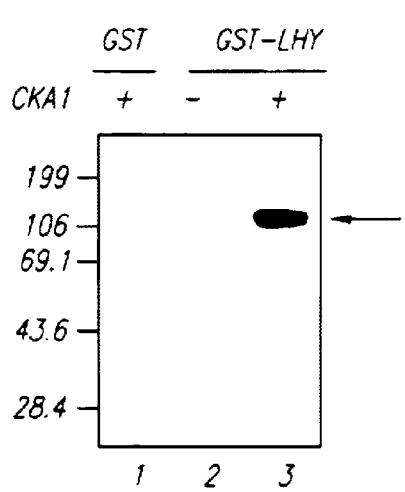
FIG. 12B illustrates phosphorylation of LHY by CK2 in vitro. GST (lane 1) or GST-LHY (lanes 2 and 3) was incubated with 280 ng of CKA1 (lanes 1 and 3) or without CKA1 (lane 2) in the presence of [γ-$^{32}$P]ATP. The arrow indicates the position of the GST-LHY protein after electrophoresis.
Figure 12C:
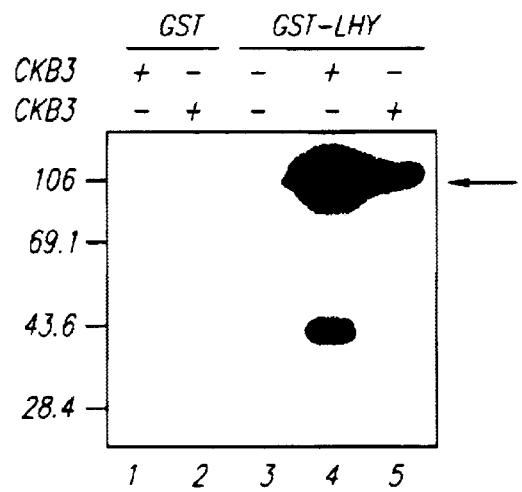
FIG. 12C shows that CK2 β-subunits enhance phosphorylation of LHY by CKA1. GST alone (lanes 1 and 2) or GST-LHY (lanes 3–5) was incubated with 14 ng of CKA1 and 35 ng of CKB1 (lanes 1 and 4) or CKB3 (lanes 2 and 5) or without β-subunits (lane 3). The arrow indicates the position of the GST-LHY protein.
Figure 13A:
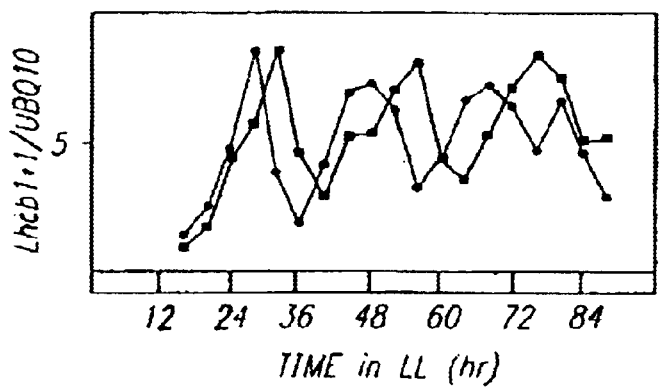
FIG. 13 shows that the periods of output genes are shortened in the CKB3-ox transgenic plants. Total RNA was isolated from wild-type and CKB3-ox (line ox18) plants grown as in FIG. 11, and expression of Lhcb1*1 (FIG. 13A), CCR2 (FIG. 13B), CAT2 (FIG. 13C) and CAT3 (FIG. 13D) RNAs was analyzed with $^{32}$P-labeled probes. The UBQ10 RNA levels were used as an internal control. Closed squares (solid line), wild-type: open circles. CKB3-ox. The bar represents the subjective light conditions for the wild-type plants. Similar results were obtained in three experiments and with another CKB3-ox (ox41) line.
Figure 13B:
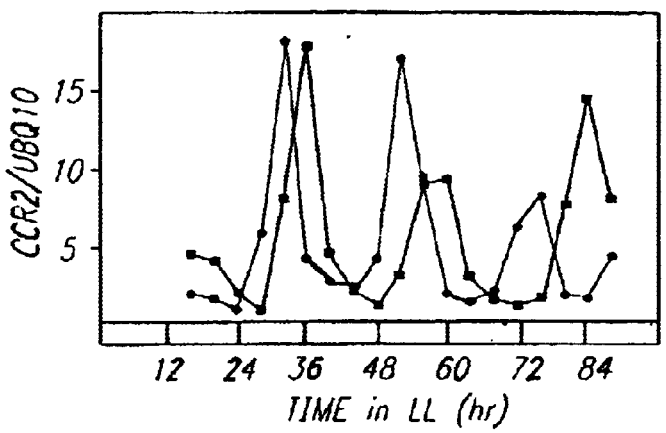
Figure 13C:
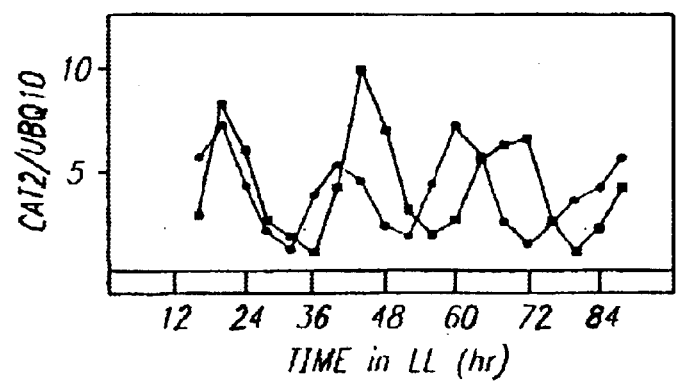
Figure 13D:
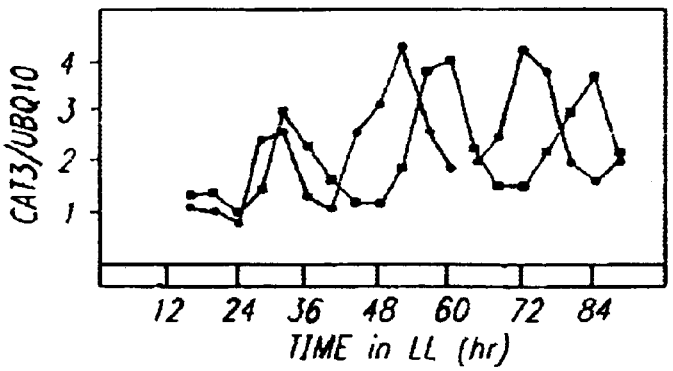

Because LHY is closely related to CCA1 both structurally and functionally (49), we tested the possibility that CK2 can also interact with and phosphorylate LHY. FIG. 12A shows that, like CCA1, LHY could bind to CKB1 and CKB3 efficiently and specifically. To make this determination a PCR fragment containing the entire LHY gene was cloned in pGEX-3X (Pharmacia). The GST-LHY fusion protein was produced and purified as described in (55, 26, 48). In vitro binding assays were performed using $^{35}$S-labeled CKB3 and glutathione-agarose beads (Sigma) with bound GST or GST-LHY. Furthermore, FIG. 12B shows that CKA1, the α-subunit of CK2, could phosphorylate LHY, and this phosphorylation was enhanced by adding either CKB1 or CKB3. In vitro kinase assays were performed using GST-LHY bound to glutathione-agarose beads and recombinant CK2α- and β-subunits as described in (55, 26, 48). These data are consistent with the idea that CK2 can interact with and phosphorylate both CCA1 and LHY in Arabidopsis.

If the function of both CCA1 and LHY is closely associated with a central oscillator and this is altered by increased CK2 activity, then the period lengths of the circadian rhythms of output genes should also be changed to reflect that of the CCA1 and LHY RNA rhythms. We therefore tested whether overexpression of CKB3 affected genes representing different rhythmic outputs of the circadian clock. Lhcb1*1 and CAT2 RNAs normally peak around subjective dawn and during the subjective day, whereas CAT3 and CCR2 RNAs peak considerably later in wild-type plants. FIG. 13 shows that overexpression of CKB3 had the same effect on the circadian expression of these genes as it did on the CCA1 and LHY RNA rhythms. Although it did not alter the amplitudes, it shortened the periods of the rhythms by about four hours.

It has been shown that the circadian clock is involved in the control of hypocotyl elongation and the photoperiodic flowering response (13). Overexpression of CKB3 did not affect hypocotyl elongation under continuous white light or dark conditions. Hypocotyl lengths of 5-day-old seedlings were measured using a digital camera (Kodak DCS 420) and the NIH image program. The average hypocotyl lengths of plants grown in continuous white light were: wild-type, 2.19±0.09 mm; CKB3-ox, 2.23±0.14 mm (line ox18) and 2.06±0.85 mm (line ox41); in the dark: wild-type, 11.6±0.28; CKB3-ox, 11.3±0.30 mm (line ox18) and 11.6±0.28 mm (line ox41). However, CKB3 overexpression did affect the photoperiodic induction of flowering. Table 1 shows that CKB3-ox lines flowered earlier than wild-type in short-day conditions, whereas CKB3 overexpression did not substantially affect flowering time in long-day conditions. To obtain data for the table plants were grown under long-day (L:D 16:8) or short-day (L:D 8:16) conditions as described in (20). the table shows the number of total leaves (including cauline leaves on the main stem) on the day when the first flower opened. Leaves of 10–20 plants were counted and values reported are means ±Standard Error. Experiments were done three times under long-day and twice under short-day conditions with similar results. Under long-day conditions both the experimental and wild type plants have nearly the same number of leaves showing that flowering response was essentially unaltered. However, under short-day conditions the wild type plants take much longer to flower growing significantly larger (more leaves) than the experimental plants. Thus, CKB3 overexpression caused a diminished photoperiodic flowering response, and while we cannot rule out other possibilities, this effect may well be a result of the altered clock function in CKB3-ox plants.

TABLE 1

|  | Long Days | Short Days |
| --- | --- | --- |
| Wild Type | 14.2 ± 0.2 | 50.3 ± 1.6 |
| CKB3-ox18 | 12.1 ± 0.2 | 28.1 ± 1.0 |
| CKB3-ox41 | 12.0 ± 0.2 | 26.9 ± 0.9 |

These data show that an increase in CK2 activity alters circadian rhythms in Arabidopsis. CK2 can interact with and phosphorylate both CCA1 and LHY, proteins that are closely associated with the central oscillator of the circadian clock. Overexpression of CKB3 substantially increased the catalytic activity of CK2 in the plant in a way similar to that seen in other organisms (47). This overexpression in Arabidopsis caused shorter periods of circadian oscillations of both CCA1 and LHY RNAs as well as those of several output genes. It also affected the timing of flowering, but did not affect hypocotyl elongation. In these respects, the CKB3-ox lines are similar to phenotypes of toc1, as both lines exhibited shorter periods of output genes, a reduced photoperiodic flowering response in the Columbia ecotype, but normal hypocotyl elongation under light and dark conditions (37, 52). Two classes of mutants which affect the input pathway, det1 and plants overexpressing phyA and phyB, also exhibited a short-period phenotype (4, 8, 38, 53). However, morphological phenotypes that are also associated with these lines are absent in the CKB3-ox and toc1 plants. Furthermore, in contrast to the higher Lhcb1*1 expression seen in the det1 and phyA/B-overexpressing lines, induction of Lhcb1*1 in CKB3-ox plants by brief red illumination was reduced compared to wild-type (data not shown). This observation is consistent with the finding that antisense expression of the CK2 α-subunit gene increased the expression of Lhcb1*1 under similar conditions (30). We conclude that CK2 affects components that are part of the central oscillator itself or closely associated with it.

Recently, mutant alleles of a clock gene, double-time (dbt), were isolated in Drosophila (29). These mutations alter the periods of behavioral rhythms and molecular oscillations of clock components PER and TIM and also affect PER phosphorylation and stability. The dbt gene encodes a protein (DBT) closely related to human casein kinase 1ε (29). Furthermore, DBT can interact with PER in vitro and in Drosophila cells, suggesting that DBT regulates PER phosphorylation directly. Both casein kinase 1ε and CK2 are Ser/Thr kinases that do not require a second messenger as a cofactor, and both prefer acidic substrates such as casein (42, 54, 24). Our finding that CK2 can interact with and phosphorylate both CCA1 and LHY in vitro is consistent with the idea that CK2 could modulate the circadian clock by direct interaction with and/or phosphorylation of the CCA1 and LHY proteins. Such interactions may control the activity and/or stability of these proteins. We have found that CCA1 and LHY can interact in vitro (data not shown) and such an interaction could also be a target for modification by CK2. Because the periods of LHY and several output genes expression were also shortened in a CCA1-null mutant line (19), we suggest that CKB3 overexpression might inactivate and/or destabilize CCA1 and LHY by altering their phosphorylation state. We cannot exclude the possibility that CKB3 affects clock components other than or in addition to CCA1 and LHY. However, the results presented here clearly demonstrate that the protein kinase CK2 is involved in the function of the circadian clock in Arabidopsis.

In summary, interaction of subunits of CK2 with CCA1 and phosphorylation of CCA1 by CK2 may modulate CCA1 activities that are required for phytochrome regulation of Lhcb1*3 gene expression and for circadian clock function. In light of the involvement of CCA1 in circadian rhythms (62), it is of particular interest that the clock gene affected in the double-time mutant of Drosophila and which is required for circadian rhythmicity has recently been cloned and found to be closely related to human casein kinase 1ε (29). While the physiological significance of the CK2-CCA1 association remains to be elucidated, our findings should be important steps toward understanding the regulation of CCA1 function in Arabidopsis.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

CITED REFERENCES

1. Allende, J. E. & Allende, C. C. (1995) FASEB J. 9, 313–323.
2. Armstrong, S. A., Barry, D. A., Leggett, R. W. & Mueller, C. R (1997) J. Biol. Chem. 272, 13489–13495.
3. Bidwai, A. P., Reed, J. C. & Glover C. V. C. (1995) J. Biol. Chem. 270, 10395–10404.
4. Boylan, M. T. and P. H. Quail, Proc. Natl. Acad. Sci. USA, 88, 10806 (1991).
5. Casnellie, J. E., Methods Enzymol, 200, 115
6. Chen, M & Cooper, J. A. (1997) Proc. Natl. Acad. Sci. USA 94, 9136–9140.

7. Chen, M., Li, D., Krebs, E. G. & Cooper, J. A. (1997) Mol. Cell. Biol. 17, 1904–1912.
8. Chory, J., C. Peto, R. Feinbaum, L. Pratt, F. Ausubel, Cell 58, 991 (1989).
9. Cochet, C., Feige, J. J., Pirollet, F., Keramidas, M. & Chambaz, E. M. (1982) Biochem. Pharmacol, 31, 1357–1361.
10. Collinge, M. A. & Walker (1994) Plant Mol. Biol. 25, 649–658.
11. Currie, R. A. (1997) J. Biol. Chem. 272, 30880–30888.
12. Datta, N. & Cashmore, A. R. (1989) Plant Cell 1, 1069–1077.
13. Dowson-Day, M. J. and A. J. Millar, Plant J. 17, 63 (1999); B. Thomas and D. Vince-Prue, Photoperiodism in Plants (Academic Press, San Diego, Calif. 1997)
14. Dunlap, J. C., Annu. Rev. Genet. 30, 579 (1996);
15. Dunlap, J. C., Cell 96, 271 (1999).
16. Dunlap, J. C., Curr. Opin. Genet. Dev. 8, 400 (1998).
17. Evans, G. I., G. K. Lewis, G. Ramsay, J. M. Bishop, Mol. Cell. Biol. 5, 3610 (1985).
18. Gonzatti-Haces, M. I. & Traugh J. A. (1982) J. Biol. Chem. 257, 6642–6645.
19. Green, R. M. and E. M. Tobin, Proc. Natl. Acad. Sci. USA 96, 4176 (1999).
20. Hanna, D. E., Rethinaswamy, A. & Glover, C. V. C. (1995) J. Biol. Chem. 43, 25905–25914.
21. Harper, J. W., Adami, G. R., Wei, N., Keyomarsi, K. & Elledge, S. J. (1993) Cell 75, 805–816.
22. Heller-Harrison, R. A. and M. P. Czech, (1991) J. Biol. Chem, 266, 14435 (1991).
23. Hicks, K. A. et al., Science 274, 790 (1996).
24. Issinger, O. -G., Pharmacol. Ther. 59, 1–30 (1993).
25. Jans, D. A. & Jans, J. (1994) Oncogene 9, 2961–2968.
26. Kay, S. A. and A. J. Millar, Cell 83, 361 (1995).
27. Kenigsbuch, D. & Tobin, E. M. (1995) Plant Physiol. 108, 1023–1027.
28. Klimezak, L. J., Schindler, U. & Cashmore, A. R. (1992) Plant Cell 4, 87–98.
29. Kloss, B., Price, J. L., Saez, L., Blau, J., Rothenfluh, A., Wesley, C. S. & Young, M. W. (1998) Cell 94, 97–107.
30. Lee, Y., A. M. Lloyd, S. J. Roux, Plant Physiol. 119, 989 (1999).
31. Leger, H., Sock, E., Renner, K., Grummt, F. & Wegner, M. Mol. Cell. Biol. 15, 3738–3747 (1995).
32. Lütcke, H. A., Chow, K. C., Mickel, F. S., Moss, K. A., Kern, H. F. & Scheele, G. A. (1987) EMBO J. 6, 43–48.
33. McClung, C. R., Trends in Plant Sci. 3, 454 (1998).
34. McElhinny, J. A., Trushin S. A., Bren, G. D., Chester N. & Paya, C. V. (1996) Mol. Cell. Biol. 16, 899–906.
35. Menkens, A. E. & Cashmore, A. R. (1994) Proc. Natl. Acad. Sci. USA 91, 2522–2526.
36. Millar, A. J. & Kay, S. A. (1997) Bio Essays 19, 209–21422.
37. Millar, A., I. A. Carré, C. S. Strayer, N. -H. Chua, S. A. Kay, Science 267, 1161 (1995).
38. Millar, A. J., M. Straume, J. Chory, N. -H. Chua, S. A. Kay, Science 267, 1163 (1995).
39. Mizoguchi, T., Yamaguchi-Shinozaki, K., Hayashida, N., Kamada, H. & Shinozaki, K. (1993) Plant Mol. Biol. 21, 279–289.
40. Molkentin, J. D., Li, L. & Olson, E. N. (1996) J. Biol. Chem. 271, 17199–17204.
41. O'Reilly, D., Hanscombe, O & O'Hare, P. (1997) EMBO J. 16, 2420–2430
42. Pinna, L. A. (1990) Biochem. Biophys. Acta 1054, 267–284.
43. Putterill, J., F. Robson, K. Lee, R. Simon, G. Coupland, Cell 80, 847 (1995).
44. Quail, P. H., Boylan, M. T., Parks, B. M., Short, T. W., Xu, Y. & Wagner, D. (1995) Science 268, 675–680.
45. Reed, J. C., Bidwai, A. P. & Glover, C. V. C. (1994) J. Biol. Chem. 269, 18192–18200.
46. Reppert, S. M., Neuron 21, 1 (1998);
47. Roussou, I. & Draetta, G. (1994) Mol. Cell. Biol. 14, 576–586.
48. Sassone-Corsi, P., Nature 392, 871 (1998).
49. Schaffer, R. et al., Cell 93, 1219 (1998).
50. Shibagaki, Y., Holmes, M. L., Appa, R. S. & Chow, S. A. (1997) Virol. 230, 1–10.
51. So. W. V. and M. Rosbash, EMBO J. 16, 7146 (1997).
52. Somers, D. E., A. A. R. Webb, M. Pearson, S. A. Kay, Development 125, 485 (1998).
53. Somers, D. E., P. F. Devlin, S. A. Kay, Science 282, 1488 (1998).
54. Songyang, Z. et al. Mol. Cell. Biol. 16, 6486 (1996).
55. Sugano, S., C. Andronis, R. M. Green, Z. -Y. Wang. E. M. Tobin, Proc. Natl. Acad. Sci. USA 95, 11020 (1998).
56. Sun, L., Doxsee, R., A., Harel, E. & Tobin, E. M. (1993) Plant Cell. 5, 109–121.
57. Suri, V., A. Lanjuin, M. Rosbash, EMBO J. 18, 675 (1999).
58. Tanaka, K., Nakafuku, M., Tamanoi, F., Kaziro, Y., Matsumoto, K. & Toh-c, A. (1990) Mol. Cell. Biol. 10. 4303–4313.
59. Tobin, E. M. & Kehoe, D., M. (1994) Sem. Cell Biol. 5, 335–346.
60. Wagner, S. & Green, M. R. (1993) Science 262, 395–399.
61. Wang, Z. -Y. et al. Plant Cell 9, 491 (1997).
62. Wang, Z. -Y. & Tobin, E. M. (1998) Cell 93, 1207–1217.
63. Wang, Z. -Y., Kenigsbuch, D., Sun, L., Harel, E., Ong, M., S. & Tobin, E. M. (1997) Plant Cell 9, 491–507.
64. Wilsbacher, L. D. and J. S. Takahashi, Curr. Opin. Genet. Dev 8, 595 (1998).
65. Young, M. W., Annu. Rev. Biochem. 67, 135 (1998).
66. Zhang, B., Chen, W., Foley, R. C., Büttner, M. & Singh, K. B. Plant Cell 7, 2241–2252.
67. Zwijsen, R. M., Wientjens, E., Klompmaker, R., van der Sman, J., Bernards, R. & Michalidias, R. J. A. M. (1997) *Cell* 88, 405–415.

We claim:

1. An isolated nucleic acid comprising the coding sequence of SEQ ID NO: 1.

2. A host cell transformed with the nucleic acid of claim 1 or a nucleic acid complementary to said nucleic acid.

3. A host cell transformed with a nucleic acid that encodes a polypeptide having the amino acid sequence of SEQ ID NO: 2.

4. A transgenic plant comprising the nucleic acid of SEQ ID NO: 1.

5. A transgenic plant comprising a nucleic acid encoding a polypeptide having the amino acid sequence of SEQ ID NO: 2.

6. A method of altering circadian rhythms and flowering in a plant comprising transforming a plant with a nucleic acid having the sequence of SEQ ID NO: 1.

7. A method of altering circadian rhythms and flowering in a plant comprising transforming the plant with a nucleic acid encoding a polypeptide having the amino acid sequence of SEQ ID NO: 2.

8. A method of altering circadian rhythms and flowering in a plant comprising transforming a plant with a nucleic acid encoding a β-subunit of protein kinase CK2 within the plant having an amino acid sequence at least 75% identical to SEQ ID NO: 2.

UNITED STATES PATENT AND TRADEMARK OFFICE
CERTIFICATE OF CORRECTION

PATENT NO. : 6,727,407 B1  Page 1 of 1
APPLICATION NO. : 09/359026
DATED : April 27, 2004
INVENTOR(S) : Elaine M. Tobin et al.

It is certified that error appears in the above-identified patent and that said Letters Patent is hereby corrected as shown below:

Column 1, paragraph beginning on line 13 should be replaced with the following paragraph:

-- This invention was made with Government support under Grant No. RO1-GM023167 awarded by the National Institutes of Health. The Government has certain rights in this invention. --

Signed and Sealed this

Tenth Day of August, 2010

David J. Kappos
*Director of the United States Patent and Trademark Office*

SEQUENCE LISTING

<160> NUMBER OF SEQ ID NOS: 11

<210> SEQ ID NO 1
<211> LENGTH: 1080
<212> TYPE: DNA
<213> ORGANISM: Arabidopsis thaliana -continued

```
<400> SEQUENCE: 1
gtcgacccac gcgtccgaga agaaaaccct agatttctcc gtctctctaa tttcctttct      60
ctctcaagct tctcagaaag tctgacactt tcgagaatct aatctccaaa tttcttgtct     120
ttttggagaa ggaatcgaat tatgtacaag gaacgtagtg gaggaggtgg tggtgggtca     180
tcgagatcag agatcctcgg tggagctatt gatcggaaac gaatcaacga tgcactcaat     240
aagaaactag agaaatcttc aacttccacc accacatcta gggttttctc ttctaaagac     300
aaagatccct ttccttcac atctactaaa actcagcttc ctgatgtgga atcggaaact      360
gatagtgaag ggtctgatgt gagtggatcg gagggtgatg atacgtcgtg gatctcttgg     420
ttttgtaatt tgagagggaa tgatttcttc tgtgaagtcg atgaagatta tattcaagat     480
gatttcaatc tttgtggttt aagtggtcaa gtcccttact atgattatgc acttgatctc     540
attttagatg ttgatgcttc caacagtgag atgtttactg atgaacagca tgaaatggtg     600
gaatcagctg ctgagatgct atatggtctt attcatgttc gttacatttt gactactaaa     660
ggaatggctg caatgactga gaagtacaag aactgtgatt tcgggagatg cccgagagtt     720
ttctgttgcg gtcagtcttg tcttccagtt ggacaatccg atatcccgag atcgagtact     780
gtgaagatat actgccctaa atgcgaggat atatcttacc cgcgatctaa attccaaggc     840
aatattgatg gagcgtactt tggaaccaca ttccctcact tgttcttgat gacttacggg     900
aacttaaagc cgcagaagcc tactcaaagc tatgtcccaa aaatctttgg cttcaaggta     960
cacaaaccat gatactagtg ctctgcattc tcaatggtga tacatttagt ggctctgtaa    1020
ttgcatccgg atgagcaact gaaacgatag ctgcggtgac tggagcatac atcaaccatt    1080

<210> SEQ ID NO 2
<211> LENGTH: 276
<212> TYPE: PRT
<213> ORGANISM: Arabidopsis thaliana

<400> SEQUENCE: 2

Met Tyr Lys Glu Arg Ser Gly Gly Gly Gly Ser Ser Arg Ser
1               5                   10                  15

Glu Ile Leu Gly Gly Ala Ile Asp Arg Lys Arg Ile Asn Asp Ala Leu
            20                  25                  30

Asn Lys Lys Leu Glu Lys Ser Ser Thr Ser Thr Thr Ser Arg Val
        35                  40                  45

Phe Ser Ser Lys Asp Lys Asp Pro Phe Ser Phe Thr Ser Lys Thr
    50                  55                  60

Gln Leu Pro Asp Val Glu Ser Glu Thr Asp Ser Glu Gly Ser Asp Val
65                  70                  75                  80

Ser Gly Ser Glu Gly Asp Asp Thr Ser Trp Ile Ser Trp Phe Cys Asn
                85                  90                  95

Leu Arg Gly Asn Asp Phe Phe Cys Glu Val Asp Glu Asp Tyr Ile Gln
            100                 105                 110

Asp Asp Phe Asn Leu Cys Gly Leu Ser Gly Gln Val Pro Tyr Tyr Asp
        115                 120                 125

Tyr Ala Leu Asp Leu Ile Leu Asp Val Asp Ala Ser Asn Ser Glu Met
    130                 135                 140

Phe Thr Asp Glu Gln His Glu Met Val Glu Ser Ala Ala Glu Met Leu
145                 150                 155                 160

Tyr Gly Leu Ile His Val Arg Tyr Ile Leu Thr Thr Lys Gly Met Ala
                165                 170                 175
```

Ala Met Thr Glu Lys Tyr Lys Asn Cys Asp Phe Gly Arg Cys Pro Arg
            180                 185                 190

Val Phe Cys Cys Gly Gln Ser Cys Leu Pro Val Gly Gln Ser Asp Ile
        195                 200                 205

Pro Arg Ser Ser Thr Val Lys Ile Tyr Cys Pro Lys Cys Glu Asp Ile
    210                 215                 220

Ser Tyr Pro Arg Ser Lys Phe Gln Gly Asn Ile Asp Gly Ala Tyr Phe
225                 230                 235                 240

Gly Thr Thr Phe Pro His Leu Phe Leu Met Thr Tyr Gly Asn Leu Lys
                245                 250                 255

Pro Gln Lys Pro Thr Gln Ser Tyr Val Pro Lys Ile Phe Gly Phe Lys
            260                 265                 270

Val His Lys Pro
        275

<210> SEQ ID NO 3
<211> LENGTH: 32
<212> TYPE: PRT
<213> ORGANISM: Unknown
<220> FEATURE:
<223> OTHER INFORMATION: potential metal-binding motif
<220> FEATURE:
<221> NAME/KEY: MISC_FEATURE
<222> LOCATION: (3)..(28)
<223> OTHER INFORMATION: X = any amino acid
<220> FEATURE:
<221> NAME/KEY: MISC_FEATURE
<222> LOCATION: (31)..(31)
<223> OTHER INFORMATION: X = any amino acid

<400> SEQUENCE: 3

Cys Pro Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Cys Pro Xaa Cys
            20                  25                  30

<210> SEQ ID NO 4
<211> LENGTH: 5
<212> TYPE: PRT
<213> ORGANISM: Unknown
<220> FEATURE:
<223> OTHER INFORMATION: conserved autophosphorylation site

<400> SEQUENCE: 4

Ser Ser Ser Glu Glu
1               5

<210> SEQ ID NO 5
<211> LENGTH: 6
<212> TYPE: PRT
<213> ORGANISM: Unknown
<220> FEATURE:
<223> OTHER INFORMATION: CK2 recognition phosphorylation site

<400> SEQUENCE: 5

Ser Gly Ser Glu Gly Asp
1               5

<210> SEQ ID NO 6
<211> LENGTH: 5
<212> TYPE: PRT
<213> ORGANISM: Unknown
<220> FEATURE:
<223> OTHER INFORMATION: CK2 recognition phosphorylation site

```
<400> SEQUENCE: 6

Ser Glu Gly Asp Asp
1               5

<210> SEQ ID NO 7
<211> LENGTH: 50
<212> TYPE: DNA
<213> ORGANISM: Unknown
<220> FEATURE:
<223> OTHER INFORMATION: c-myc Bgl-II site

<400> SEQUENCE: 7
aattgagatc tcatggagca aaagcttatc agcgaggagg acttgaacat            50

<210> SEQ ID NO 8
<211> LENGTH: 49
<212> TYPE: DNA
<213> ORGANISM: Unknown
<220> FEATURE:
<223> OTHER INFORMATION: c-myc Bgl-II site

<400> SEQUENCE: 8
gtacatgttc aagtcctcct cgctgataag cttttgctcc atgagatct             49

<210> SEQ ID NO 9
<211> LENGTH: 24
<212> TYPE: DNA
<213> ORGANISM: Artificial Sequence
<220> FEATURE:
<223> OTHER INFORMATION: CKB3 primer

<400> SEQUENCE: 9
acaaggaacg tagtggagga ggtg                                        24

<210> SEQ ID NO 10
<211> LENGTH: 23
<212> TYPE: DNA
<213> ORGANISM: Artificial Sequence
<220> FEATURE:
<223> OTHER INFORMATION: CKB3 primer

<400> SEQUENCE: 10
aaccctagat gtggtggtgg aag                                         23

<210> SEQ ID NO 11
<211> LENGTH: 10
<212> TYPE: PRT
<213> ORGANISM: Artificial Sequence
<220> FEATURE:
<223> OTHER INFORMATION: Specific peptide substrate

<400> SEQUENCE: 11

Arg Arg Arg Asp Asp Asp Ser Asp Asp Asp
1               5                   10
```